US012377139B2

United States Patent
Faburay et al.

(10) Patent No.: US 12,377,139 B2
(45) Date of Patent: Aug. 5, 2025

(54) EHRLICHIA RUMINANTIUM IMMUNOGENIC COMPOSITIONS AND METHODS OF USING THEREOF

(71) Applicant: Kansas State University Research Foundation, Manhattan, KS (US)

(72) Inventors: Bonto Faburay, Manhattan, KS (US); Jodi McGill, Manhattan, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 0 days.

(21) Appl. No.: 16/630,212

(22) PCT Filed: Jul. 12, 2018

(86) PCT No.: PCT/US2018/041863
§ 371 (c)(1),
(2) Date: Jan. 10, 2020

(87) PCT Pub. No.: WO2019/014469
PCT Pub. Date: Jan. 17, 2019

(65) Prior Publication Data
US 2020/0129604 A1    Apr. 30, 2020

Related U.S. Application Data

(60) Provisional application No. 62/531,697, filed on Jul. 12, 2017.

(51) Int. Cl.
*A61K 39/02* (2006.01)
*A61K 9/00* (2006.01)
*A61K 39/39* (2006.01)
*A61P 31/04* (2006.01)
*C07K 14/29* (2006.01)
*A61K 39/00* (2006.01)

(52) U.S. Cl.
CPC ........ *A61K 39/0233* (2013.01); *A61K 9/0019* (2013.01); *A61K 39/39* (2013.01); *A61P 31/04* (2018.01); *C07K 14/29* (2013.01); *A61K 2039/54* (2013.01); *A61K 2039/545* (2013.01); *A61K 2039/55566* (2013.01); *C07K 2319/02* (2013.01)

(58) Field of Classification Search
CPC . A61K 39/0233; A61K 39/39; C07K 2319/02
USPC ....................... 424/93.1, 184.1, 185.1, 278.1
See application file for complete search history.

(56) References Cited

U.S. PATENT DOCUMENTS

| | | | | |
|---|---|---|---|---|
| 2004/0265333 A1* | 12/2004 | Rikihisa | ................ | C07K 14/29 424/190.1 |
| 2005/0142557 A1* | 6/2005 | Alleman | ............ | C07K 16/1246 435/6.16 |
| 2008/0274134 A1* | 11/2008 | Schulke | ................ | A61K 39/12 424/196.11 |
| 2009/0075368 A1* | 3/2009 | Rikihisa | ................ | C07K 14/29 435/320.1 |
| 2011/0033487 A1* | 2/2011 | McBride | ................ | A61P 31/04 514/21.3 |
| 2013/0121915 A1* | 5/2013 | Paas | ..................... | C07K 14/245 424/9.1 |
| 2014/0121125 A1* | 5/2014 | Mehra | .................... | C07K 14/29 506/9 |
| 2016/0106825 A1* | 4/2016 | Thomas | ............ | A61K 39/0233 424/234.1 |

OTHER PUBLICATIONS

Van Vliet et al. Infection and Immunity, Apr. 1994, vol. 62, No. 4, p. 1451-1456.*
Nyika et al. Vaccine 20 (2002) 1215-1225.*
"Fast Facts Heartwater" retrieved from May 25, 2022 https://www.cfsph.iastate.edu/FastFacts/pdfs/heartwater_F.pdf Apr. 2008.*
Postigo et al. Veterinary Microbiology vol. 126, issues 1-2, Apr. 2008, pp. 136-147.*
Juliant et al. Methods Mol Biol (2013) 988:59-77.*
Reddy et al. Clinical and Diagnostic Laboratory Immunology, vol. 3, No. 4, Jul. 1996, p. 417-422.*

* cited by examiner

*Primary Examiner* — Oluwatosin A Ogunbiyi
(74) *Attorney, Agent, or Firm* — Sandberg Phoenix & von Gontard, PC; Tracey S. Truitt

(57) ABSTRACT

The present disclosure provides compositions and methods for reducing the incidence of and/or severity of diseases associated with tick-borne pathogens. In preferred forms, the compositions comprise a recombinant antigenic protein subunit that has been glycosylated. Some preferred subunits include the MAP1 protein of *Ehrlichia ruminantium*, the p30-1 sequence from *Ehrlichia canis*, the p28-Omp19 protein from *Ehrlichia chaffeensis*, and the MSP4 protein from *Anaplasma marginale*. Administration of such compositions to an animal in need thereof provides protection against clinical signs of infection in susceptible animals.

12 Claims, 20 Drawing Sheets
Specification includes a Sequence Listing.

Fig. 1

| | | |
|---|---|---|
| Antigua | MNCKKIFITSTLISLVSHLPGVSFSDVIQEDSSPVGSVVIISAKYMPTASHFGKMSIKEDS | 60 |
| Gardel  | MNCKKIFITSTLISLVSHLPGVSFSDVIQEDSSPAGSVVIISAKYMPTASHFGKMSIKEDS | 60 |
|         | ************************************************************ | |

| | | |
|---|---|---|
| Antigua | RDTKVVFGLKKDWDGVKTSSS-----NTIFTEKDYSFKYENNPFLGFAGAIGYSMNGPRI | 115 |
| Gardel  | KNTQTVFGLKKDWDGVKTPSSDSGMNSIIFTEKDYSFKYENNPFLGFAGAIGYSMNGPRI | 120 |
|         | :.*:************:    *:*********************:****  | |

| | | |
|---|---|---|
| Antigua | EFEISYETFDVKNPGGNYKNDAHMYCALDTATS--SGGAAASTSVMVKNENLTDISLMLN | 173 |
| Gardel  | EFEVSYETFDVKNPGGNYKNDAHMYCALDTGTPGSTQGATLNSSVMVKNENLTDIALMLN | 180 |
|         | *:*********************: .:*.:.*.*:*******::*** | |

| | | |
|---|---|---|
| Antigua | ACYDIMLDGMPVSPYVCAGIGTDLVSVINSTNPKLSYQGKLGISYSINPEASIFIGGHFH | 233 |
| Gardel  | ACYDITLEGMPVSPYVCAGIGTDLVSVINATNPKLSYQGKLGISYSINPEASIFIGGHFH | 240 |
|         | *****:*:******************:************************* | |

| | | |
|---|---|---|
| Antigua | RVIGNEFKDITTSKIFNTSN--TGGATPGFASAILDVCHFGIEIGGRFVF | 281 |
| Gardel  | RVIGNEFKDITTSKIFTSTGKLATAASPGFASATLDVCHFGIEIGGRFVF | 290 |
|         | ***************. :  . :*.:****:************* | |

Fig. 6A
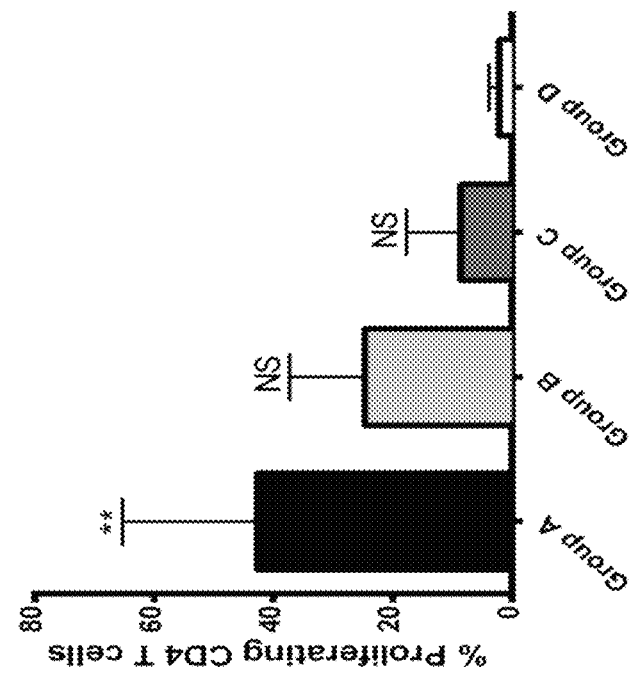
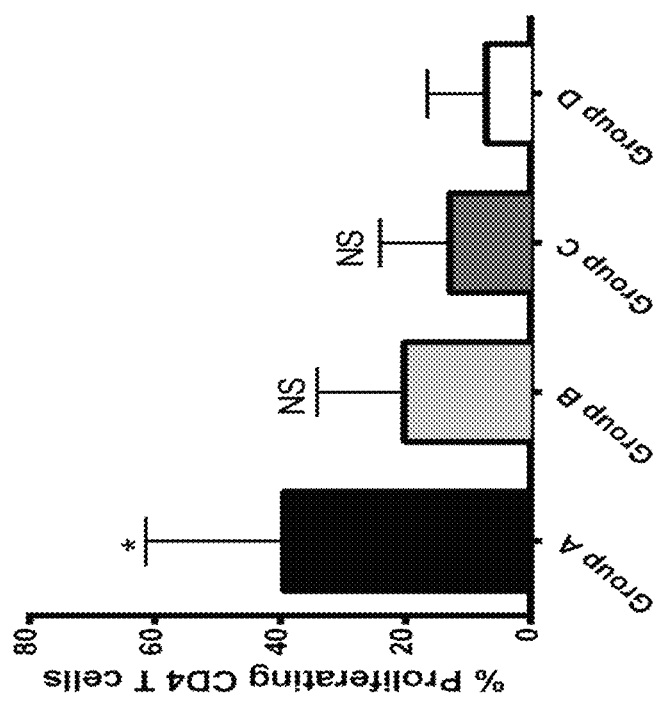

SEQUENCE LISTING

<160> NUMBER OF SEQ ID NOS: 14

<210> SEQ ID NO 1
<211> LENGTH: 789
<212> TYPE: DNA
<213> ORGANISM: Ehrlichia ruminantium

<400> SEQUENCE: 1

```
ttacctggtg tgtccttttc tgatgtaata caggaagaca gcagcccagt aggtagtgtt      60
tacatcagtg caaaatacat gccaactgct tcacattttg gtaaaatgtc aattaaagaa     120
gattctagag atactaaagt agtatttggt ctaaaaaaag attgggatgg agttaaaaca     180
agtagtagca atacaatttt cactgaaaaa gattattctt ttaaatatga aaataatcca     240
ttcttaggtt ttgctggagc aattggatac tcaatgaatg gtccaagaat agaatttgaa     300
atatcctatg aaacttttga tgtaaaaaac ccaggtggta actataaaaa tgatgcccat     360
atgtattgtg ccttagacac agcaacatca tctggtggag cagcagcaag tacatctgtt     420
atggtaaaaa atgaaaattt aacagatata tcattaatgt taaatgcatg ttatgatata     480
atgcttgatg gaatgccagt gtctccatat gtatgtgcag gtattggtac cgatttagtg     540
tcagtaatta attctacaaa tcctaaatta tcctatcaag aaaacttgg tataagttat       600 tcgataaatc agaagcatc tatatttatt ggcggacatt ttcatagagt tataggtaat       660
gagttcaaag atattactac ttctaagatt tttaatacta gtaacactgg tggtgccact     720
ccaggctttg catcagcaat acttgatgtc tgccatttcg gtatagaaat tggaggaagg     780
tttgtatttt                                                           789

<210> SEQ ID NO 2
<211> LENGTH: 843
<212> TYPE: DNA
<213> ORGANISM: Ehrlichia ruminantium

<400> SEQUENCE: 2
atgaattgca agaaaatttt tatcacaagt acactaatat cattagtgtc atttttacct      60
ggtgtgtcct ttctgatgt aatacaggaa gacagcagcc agtaggtag tgtttacatc       120 agtgcaaaat acatgccaac tgcttcacat tttggtaaaa tgtcaattaa agaagattct     180
agagatacta aagtagtatt tggtctaaaa aaagattggg atggagttaa acaagtagt      240 agcaatacaa ttttcactga aaaagattat tcttttaaat atgaaaataa tccattctta     300
ggttttgctg gagcaattgg atactcaatg aatggtccaa gaatagaatt tgaaatatcc     360
tatgaaactt ttgatgtaaa aaacccaggt ggtaactata aaaatgatgc ccatatgtat     420
tgtgccttag acacagcaac atcatctggt ggagcagcag caagtacatc tgttatggta     480
aaaaatgaaa atttaacaga tatatcatta atgttaaatg catgttatga taatgcttt     540 gatggaatgc cagtgtctcc atatgtatgt gcaggtattg gtaccgattt agtgtcagta     600
attaattcta caaatcctaa attatcctat caaggaaaac ttggtataag ttattcgata     660
aatccagaag catctatatt tattggcgga cattttcata gagttatagg taatgagttc     720
aaagatatta ctacttctaa gatttttaat actagtaaca ctggtggtgc cactccaggc     780
tttgcatcag caatacttga tgtctgccat ttcggtatag aaattggagg aaggtttgta     840
ttt                                                                  843

<210> SEQ ID NO 3
<211> LENGTH: 263
<212> TYPE: PRT
<213> ORGANISM: Ehrlichia ruminantium

<400> SEQUENCE: 3

Leu Pro Gly Val Ser Phe Ser Asp Val Ile Gln Glu Asp Ser Ser Pro
  1               5                  10                  15

Val Gly Ser Val Tyr Ile Ser Ala Lys Tyr Met Pro Thr Ala Ser His
             20                  25                  30
```

```
Phe Gly Lys Met Ser Ile Lys Glu Asp Ser Arg Asp Thr Lys Val Val
            35                  40                  45

Phe Gly Leu Lys Lys Asp Trp Asp Gly Val Lys Thr Ser Ser Ser Asn
 50                  55                  60

Thr Ile Phe Thr Glu Lys Asp Tyr Ser Phe Lys Tyr Glu Asn Asn Pro
 65                  70                  75                  80

Phe Leu Gly Phe Ala Gly Ala Ile Gly Tyr Ser Met Asn Gly Pro Arg
                85                  90                  95

Ile Glu Phe Glu Ile Ser Tyr Glu Thr Phe Asp Val Lys Asn Pro Gly
                100                 105                 110

Gly Asn Tyr Lys Asn Asp Ala His Met Tyr Cys Ala Leu Asp Thr Ala
            115                 120                 125

Thr Ser Ser Gly Gly Ala Ala Ala Ser Thr Ser Val Met Val Lys Asn
130                 135                 140

Glu Asn Leu Thr Asp Ile Ser Leu Met Leu Asn Ala Cys Tyr Asp Ile
145                 150                 155                 160

Met Leu Asp Gly Met Pro Val Ser Pro Tyr Val Cys Ala Gly Ile Gly
                165                 170                 175

Thr Asp Leu Val Ser Val Ile Asn Ser Thr Asn Pro Lys Leu Ser Tyr
                180                 185                 190

Gln Gly Lys Leu Gly Ile Ser Tyr Ser Ile Asn Pro Glu Ala Ser Ile
            195                 200                 205

Phe Ile Gly Gly His Phe His Arg Val Ile Gly Asn Glu Phe Lys Asp
210                 215                 220

Ile Thr Thr Ser Lys Ile Phe Asn Thr Ser Asn Thr Gly Gly Ala Thr
225                 230                 235                 240

Pro Gly Phe Ala Ser Ala Ile Leu Asp Val Cys His Phe Gly Ile Glu
                245                 250                 255

Ile Gly Gly Arg Phe Val Phe
            260
```

<210> SEQ ID NO 4
<211> LENGTH: 281
<212> TYPE: PRT
<213> ORGANISM: Ehrlichia ruminantium

<400> SEQUENCE: 4

```
Met Asn Cys Lys Lys Ile Phe Ile Thr Ser Thr Leu Ile Ser Leu Val
 1               5                  10                  15

Ser Phe Leu Pro Gly Val Ser Pro Ser Asp Val Ile Gln Glu Asp Ser
                20                  25                  30

Ser Pro Val Gly Ser Val Tyr Ile Ser Ala Lys Tyr Met Pro Thr Ala
            35                  40                  45

Ser His Phe Gly Lys Met Ser Ile Lys Glu Asp Ser Arg Asp Thr Lys
 50                  55                  60

Val Val Phe Gly Leu Lys Lys Asp Trp Asp Gly Val Lys Thr Ser Ser
 65                  70                  75                  80

Ser Asn Thr Ile Phe Thr Glu Lys Asp Tyr Ser Phe Lys Tyr Glu Asn
                85                  90                  95

Asn Pro Phe Leu Gly Phe Ala Gly Ala Ile Gly Tyr Ser Met Asn Gly
                100                 105                 110

Pro Arg Ile Glu Phe Glu Ile Ser Tyr Glu Thr Phe Asp Val Lys Asn
            115                 120                 125

Pro Gly Gly Asn Tyr Lys Asn Asp Ala His Met Tyr Cys Ala Leu Asp
```

```
                    130                 135                 140
Thr Ala Thr Ser Ser Gly Gly Ala Ala Ala Ser Thr Ser Val Met Val
145                 150                 155                 160

Lys Asn Glu Asn Leu Thr Asp Ile Ser Leu Met Leu Asn Ala Cys Tyr
                165                 170                 175

Asp Ile Met Leu Asp Gly Met Pro Val Ser Pro Tyr Val Cys Ala Gly
            180                 185                 190

Ile Gly Thr Asp Leu Val Ser Val Ile Asn Ser Thr Asn Pro Lys Leu
                195                 200                 205

Ser Tyr Gln Gly Lys Leu Gly Ile Ser Tyr Ser Ile Asn Pro Glu Ala
            210                 215                 220

Ser Ile Phe Ile Gly Gly His Phe His Arg Val Ile Gly Asn Glu Phe
225                 230                 235                 240

Lys Asp Ile Thr Thr Ser Lys Ile Phe Asn Thr Ser Asn Thr Gly Gly
                245                 250                 255

Ala Thr Pro Gly Phe Ala Ser Ala Ile Leu Asp Val Cys His Phe Gly
            260                 265                 270

Ile Glu Ile Gly Gly Arg Phe Val Phe
                275                 280

<210> SEQ ID NO 5
<211> LENGTH: 278
<212> TYPE: PRT
<213> ORGANISM: Ehrlichia canis

<400> SEQUENCE: 5

Met Asn Cys Lys Lys Ile Leu Ile Thr Thr Ala Leu Ile Ser Leu Met
1               5                   10                  15

Tyr Ser Ile Pro Ser Ile Ser Phe Ser Asp Thr Ile Gln Asp Gly Asn
                20                  25                  30

Met Gly Gly Asn Phe Tyr Ile Ser Gly Lys Tyr Val Pro Ser Val Ser
            35                  40                  45

His Phe Gly Ser Phe Ser Ala Lys Glu Glu Ser Lys Ser Thr Val Gly
        50                  55                  60

Val Phe Gly Leu Lys His Asp Trp Asp Gly Ser Pro Ile Leu Lys Asn
65                  70                  75                  80

Lys His Ala Asp Phe Thr Val Pro Asn Tyr Ser Phe Arg Tyr Glu Asn
                85                  90                  95

Asn Pro Phe Leu Gly Phe Ala Gly Ala Ile Gly Tyr Ser Met Gly Gly
            100                 105                 110

Pro Arg Ile Glu Phe Glu Ile Ser Tyr Glu Ala Phe Asp Val Lys Ser
        115                 120                 125

Pro Asn Ile Asn Tyr Gln Asn Asp Ala His Arg Tyr Cys Ala Leu Ser
    130                 135                 140

His His Thr Ser Ala Ala Met Glu Ala Asp Lys Phe Val Phe Leu Lys
145                 150                 155                 160

Asn Glu Gly Leu Ile Asp Ile Ser Leu Ala Ile Asn Ala Cys Tyr Asp
                165                 170                 175

Ile Ile Asn Asp Lys Val Pro Val Ser Pro Tyr Ile Cys Ala Gly Ile
            180                 185                 190

Gly Thr Asp Leu Ile Ser Met Phe Glu Ala Thr Ser Pro Lys Ile Ser
        195                 200                 205

Tyr Gln Gly Lys Leu Gly Ile Ser Tyr Ser Ile Asn Pro Glu Thr Ser
    210                 215                 220
```

-continued

```
Val Phe Ile Gly Gly His Phe His Arg Ile Ile Gly Asn Glu Phe Arg
225                 230                 235                 240

Asp Ile Pro Ala Ile Val Pro Ser Asn Ser Thr Thr Ile Ser Gly Pro
                245                 250                 255

Gln Phe Ala Thr Val Thr Leu Asn Val Cys His Phe Gly Leu Glu Leu
            260                 265                 270

Gly Gly Arg Phe Asn Phe
        275
```

<210> SEQ ID NO 6
<211> LENGTH: 281
<212> TYPE: PRT
<213> ORGANISM: Ehrlichia chaffeensis

<400> SEQUENCE: 6

```
Met Asn Tyr Lys Lys Val Phe Ile Thr Ser Ala Leu Ile Ser Leu Ile
1               5                   10                  15

Ser Ser Leu Pro Gly Val Ser Phe Ser Asp Pro Ala Gly Ser Gly Ile
            20                  25                  30

Asn Gly Asn Phe Tyr Ile Ser Gly Lys Tyr Met Pro Ser Ala Ser His
        35                  40                  45

Phe Gly Val Phe Ser Ala Lys Glu Glu Arg Asn Thr Thr Val Gly Val
50                  55                  60

Phe Gly Leu Lys Gln Asn Trp Asp Gly Ser Ala Ile Ser Asn Ser Ser
65                  70                  75                  80

Pro Asn Asp Val Phe Thr Val Ser Asn Tyr Ser Phe Lys Tyr Glu Asn
                85                  90                  95

Asn Pro Phe Leu Gly Phe Ala Gly Ala Ile Gly Tyr Ser Met Asp Gly
            100                 105                 110

Pro Arg Ile Glu Leu Glu Val Ser Tyr Glu Thr Phe Asp Val Lys Asn
        115                 120                 125

Gln Gly Asn Asn Tyr Lys Asn Glu Ala His Arg Tyr Cys Ala Leu Ser
130                 135                 140

His Asn Ser Ala Ala Asp Met Ser Ser Ala Ser Asn Asn Phe Val Phe
145                 150                 155                 160

Leu Lys Asn Glu Gly Leu Leu Asp Ile Ser Phe Met Leu Asn Ala Cys
                165                 170                 175

Tyr Asp Val Val Gly Glu Gly Ile Pro Phe Ser Pro Tyr Ile Cys Ala
            180                 185                 190

Gly Ile Gly Thr Asp Leu Val Ser Met Phe Glu Ala Thr Asn Pro Lys
        195                 200                 205

Ile Ser Tyr Gln Gly Lys Leu Gly Leu Ser Tyr Ser Ile Ser Pro Glu
210                 215                 220

Ala Ser Val Phe Ile Gly Gly His Phe His Lys Val Ile Gly Asn Glu
225                 230                 235                 240

Phe Arg Asp Ile Pro Thr Ile Ile Pro Thr Gly Ser Thr Leu Ala Gly
                245                 250                 255

Lys Gly Asn Tyr Pro Ala Ile Val Ile Leu Asp Val Cys His Phe Gly
            260                 265                 270

Ile Glu Leu Gly Gly Arg Phe Ala Phe
        275                 280
```

<210> SEQ ID NO 7
<211> LENGTH: 282
<212> TYPE: PRT
<213> ORGANISM: Anaplasma marginale

<400> SEQUENCE: 7

Met Asn Tyr Arg Glu Leu Phe Thr Gly Gly Leu Ser Ala Ala Thr Val
1               5                   10                  15

Cys Ala Cys Ser Leu Leu Val Ser Gly Ala Val Val Ala Ser Pro Met
            20                  25                  30

Ser His Glu Val Ala Ser Glu Gly Gly Val Met Gly Gly Ser Phe Tyr
        35                  40                  45

Val Gly Ala Ala Tyr Ser Pro Ala Phe Pro Ser Val Thr Ser Phe Asp
50                  55                  60

Met Arg Glu Ser Ser Lys Glu Thr Ser Tyr Val Arg Gly Tyr Asp Lys
65                  70                  75                  80

Ser Ile Ala Thr Ile Asp Val Ser Val Pro Ala Asn Phe Ser Lys Ser
                85                  90                  95

Gly Tyr Thr Phe Ala Phe Ser Lys Asn Leu Ile Thr Ser Phe Asp Gly
            100                 105                 110

Ala Val Gly Tyr Ser Leu Gly Gly Ala Arg Val Glu Leu Glu Ala Ser
        115                 120                 125

Tyr Arg Arg Phe Ala Thr Leu Ala Asp Gly Gln Tyr Ala Lys Ser Gly
130                 135                 140

Ala Glu Ser Leu Ala Ala Ile Thr Arg Asp Ala Asn Ile Thr Glu Thr
145                 150                 155                 160

Asn Tyr Phe Val Val Lys Ile Asp Glu Ile Thr Asn Thr Ser Val Met
                165                 170                 175

Leu Asn Gly Cys Tyr Asp Val Leu His Thr Asp Leu Pro Val Ser Pro
            180                 185                 190

Tyr Val Cys Ala Gly Ile Gly Ala Ser Phe Val Asp Ile Ser Lys Gln
        195                 200                 205

Val Thr Thr Lys Leu Ala Tyr Arg Gly Lys Val Gly Ile Ser Tyr Gln
210                 215                 220

Phe Thr Pro Glu Ile Ser Leu Val Ala Gly Phe Tyr His Gly Leu
225                 230                 235                 240

Phe Asp Glu Ser Tyr Lys Asp Ile Pro Ala His Asn Ser Val Lys Phe
                245                 250                 255

Ser Gly Glu Ala Lys Ala Ser Val Lys Ala His Ile Ala Asp Tyr Gly
            260                 265                 270

Phe Asn Leu Gly Ala Arg Phe Leu Phe Ser
            275                 280

<210> SEQ ID NO 8
<211> LENGTH: 34
<212> TYPE: DNA
<213> ORGANISM: Artificial Sequence
<220> FEATURE:
<223> OTHER INFORMATION: gene-specific primer BYF101F

<400> SEQUENCE: 8
caccatgaac tgcaagaaga tcttcatcac ctcc        34

<210> SEQ ID NO 9
<211> LENGTH: 30
<212> TYPE: DNA
<213> ORGANISM: Artificial Sequence
<220> FEATURE:
<223> OTHER INFORMATION: gene specific primer BYF102R

<400> SEQUENCE: 9

```
gaacacgaaa cgaccaccga tctcgatacc                                        30
```

<210> SEQ ID NO 10
<211> LENGTH: 816
<212> TYPE: DNA
<213> ORGANISM: Ehrlichia ruminantium

<400> SEQUENCE: 10

```
ttacctggtg tgtccttttc tgatgtaata caggaagata gcagcccagc aggtagtgtt       60
tacattagcg caaaatacat gccaactgca tcacattttg gtaaaatgtc aatcaaagaa      120
gattcaaaaa atactcaaac agtatttggc ctaaaaaaag attgggatgg cgttaaaaca      180
ccatcatcag atagcggtaa caatagtatt atcttcactg aaaagacta ttcattcaaa       240
tatgaaaaca acccattttt aggttttgct ggagcaattg gtattcaat gaatggtcca       300
agaatagaat ttgaagtatc ttatgaaact tttgatgtaa aaacccagg tggtaattat        360
aaaaatgatg cacatatgta ttgtgctcta gatacaggaa caccaggatc tactcagggt      420
gcaacattaa attcatctgt tatggtaaaa aatgaaaatt taactgatat tgcactaatg      480
ttaaatgcat gctatgatat aacacttgaa ggaatgccag tttctccata tgtgtgtgca      540
ggcattggta ctgattagt gtcagtaatc aatgctacaa atcctaagtt atcttatcag       600
ggaaagttag gtattagtta ttcaataaat cctgaagctt ctatctttat tggtggacat      660
ttccatagag ttataggtaa tgaatttaaa gacattacta cttccaaaat attcacctca      720
actggtaaat tagctactgc agctagccca ggttttgcat cagcaacact tgatgtttgc      780
catttcggta tagaaattgg aggaaggttt gtattt                                816
```

<210> SEQ ID NO 11
<211> LENGTH: 870
<212> TYPE: DNA
<213> ORGANISM: Ehrlichia ruminantium

<400> SEQUENCE: 11

```
atgaattgca agaaaatttt tatcacaagt acactaatat cattagtgtc attttacct        60
ggtgtgtcct tttctgatgt aatacaggaa gatagcagcc cagcaggtag tgtttacatt      120
agcgcaaaat acatgccaac tgcatcacat tttggtaaaa tgtcaatcaa agaagattca      180
aaaaatactc aaacagtatt tggcctaaaa aaagattggg atggcgttaa acaccatca       240
tcagatagcg gtaacaatag tattatcttc actgaaaaag actattcatt caaatatgaa      300
aacaacccat ttttaggttt tgctggagca attgggtatt caatgaatgg tccaagaata      360
gaatttgaag tatcttatga aacttttgat gtaaaaaacc caggtggtaa ttataaaaat      420
gatgcacata tgtattgtgc tctagataca ggaacaccag gatctactca gggtgcaaca      480
ttaaattcat ctgttatggt aaaaaatgaa aatttaactg atattgcact aatgttaaat      540
gcatgctatg atataacact tgaaggaatg ccagtttctc catatgtgtg tgcaggcatt      600
ggtactgatt tagtgtcagt aatcaatgct acaaatccta gttatcttat tcagggaaag      660
ttaggtatta gttattcaat aaatcctgaa gcttctatct ttattggtgg acatttccat      720
agagttatag gtaatgaatt taaagacatt actacttcca aaatattcac ctcaactggt      780
aaattagcta ctgcagctag cccaggtttt gcatcagcaa cacttgatgt tgccatttc      840
ggtatagaaa ttggaggaag gtttgtattt                                        870
```

<210> SEQ ID NO 12
<211> LENGTH: 273

<212> TYPE: PRT
<213> ORGANISM: Ehrlichia ruminantium

<400> SEQUENCE: 12

```
Phe Leu Pro Gly Val Ser Phe Ser Asp Val Ile Gln Glu Asp Ser Ser
1               5                   10                  15

Pro Ala Gly Ser Val Tyr Ile Ser Ala Lys Tyr Met Pro Thr Ala Ser
            20                  25                  30

His Phe Gly Lys Met Ser Ile Lys Glu Asp Ser Lys Asn Thr Gln Thr
        35                  40                  45

Val Phe Gly Leu Lys Lys Asp Trp Asp Gly Val Lys Thr Pro Ser Ser
    50                  55                  60

Asp Ser Gly Asn Asn Ser Ile Ile Phe Thr Glu Lys Asp Tyr Ser Phe
65                  70                  75                  80

Lys Tyr Glu Asn Asn Pro Phe Leu Gly Phe Ala Gly Ala Ile Gly Tyr
                85                  90                  95

Ser Met Asn Gly Pro Arg Ile Glu Phe Glu Val Ser Tyr Glu Thr Phe
            100                 105                 110

Asp Val Lys Asn Pro Gly Gly Asn Tyr Lys Asn Asp Ala His Met Tyr
        115                 120                 125

Cys Ala Leu Asp Thr Gly Thr Pro Gly Ser Thr Gln Gly Ala Thr Leu
    130                 135                 140

Asn Ser Ser Val Met Val Lys Asn Glu Asn Leu Thr Asp Ile Ala Leu
145                 150                 155                 160

Met Leu Asn Ala Cys Tyr Asp Ile Thr Leu Glu Gly Met Pro Val Ser
                165                 170                 175

Pro Tyr Val Cys Ala Gly Ile Gly Thr Asp Leu Val Ser Val Ile Asn
            180                 185                 190

Ala Thr Asn Pro Lys Leu Ser Tyr Gln Gly Lys Leu Gly Ile Ser Tyr
        195                 200                 205

Ser Ile Asn Pro Glu Ala Ser Ile Phe Ile Gly Gly His Phe His Arg
    210                 215                 220

Val Ile Gly Asn Glu Phe Lys Asp Ile Thr Thr Ser Lys Ile Phe Thr
225                 230                 235                 240

Ser Thr Gly Lys Leu Ala Thr Ala Ala Ser Pro Gly Phe Ala Ser Ala
                245                 250                 255

Thr Leu Asp Val Cys His Phe Gly Ile Glu Ile Gly Gly Arg Phe Val
            260                 265                 270

Phe
```

<210> SEQ ID NO 13
<211> LENGTH: 290
<212> TYPE: PRT
<213> ORGANISM: Ehrlichia ruminantium

<400> SEQUENCE: 13

```
Met Asn Cys Lys Lys Ile Phe Ile Thr Ser Thr Leu Ile Ser Leu Val
1               5                   10                  15

Ser Phe Leu Pro Gly Val Ser Phe Ser Asp Val Ile Gln Glu Asp Ser
            20                  25                  30

Ser Pro Ala Gly Ser Val Tyr Ile Ser Ala Lys Tyr Met Pro Thr Ala
        35                  40                  45

Ser His Phe Gly Lys Met Ser Ile Lys Glu Asp Ser Lys Asn Thr Gln
    50                  55                  60

Thr Val Phe Gly Leu Lys Lys Asp Trp Asp Gly Val Lys Thr Pro Ser
```

```
                    65                  70                  75                  80
Ser Asp Ser Gly Asn Asn Ser Ile Ile Phe Thr Glu Lys Asp Tyr Ser
                        85                  90                  95

Phe Lys Tyr Glu Asn Asn Pro Phe Leu Gly Phe Ala Gly Ala Ile Gly
                100                 105                 110

Tyr Ser Met Asn Gly Pro Arg Ile Glu Phe Glu Val Ser Tyr Glu Thr
                115                 120                 125

Phe Asp Val Lys Asn Pro Gly Gly Asn Tyr Lys Asn Asp Ala His Met
            130                 135                 140

Tyr Cys Ala Leu Asp Thr Gly Thr Pro Gly Ser Thr Gln Gly Ala Thr
145                 150                 155                 160

Leu Asn Ser Ser Val Met Val Lys Asn Glu Asn Leu Thr Asp Ile Ala
                165                 170                 175

Leu Met Leu Asn Ala Cys Tyr Asp Ile Thr Leu Glu Gly Met Pro Val
                180                 185                 190

Ser Pro Tyr Val Cys Ala Gly Ile Gly Thr Asp Leu Val Ser Val Ile
                195                 200                 205

Asn Ala Thr Asn Pro Lys Leu Ser Tyr Gln Gly Lys Leu Gly Ile Ser
            210                 215                 220

Tyr Ser Ile Asn Pro Glu Ala Ser Ile Phe Ile Gly Gly His Phe His
225                 230                 235                 240

Arg Val Ile Gly Asn Glu Phe Lys Asp Ile Thr Thr Ser Lys Ile Phe
                245                 250                 255

Thr Ser Thr Gly Lys Leu Ala Thr Ala Ala Ser Pro Gly Phe Ala Ser
                260                 265                 270

Ala Thr Leu Asp Val Cys His Phe Gly Ile Glu Ile Gly Gly Arg Phe
            275                 280                 285

Val Phe
    290

<210> SEQ ID NO 14
<211> LENGTH: 18
<212> TYPE: PRT
<213> ORGANISM: Ehrlichia ruminantium

<400> SEQUENCE: 14

Met Asn Cys Lys Lys Ile Phe Ile Thr Ser Thr Leu Ile Ser Leu Val
1               5                   10                  15

Ser Phe
```

EHRLICHIA RUMINANTIUM IMMUNOGENIC COMPOSITIONS AND METHODS OF USING THEREOF

CROSS REFERENCE TO RELATED APPLICATIONS

The current patent application is related to U.S. Patent Application Ser. No. 62/533,550, which is hereby incorporated by reference in its entirety.

SEQUENCE LISTING

This application contains a sequence listing (40432-PCT_ST25.txt, 22, 400 bytes) in computer readable format, the teachings and content of which are hereby incorporated by reference.

BACKGROUND OF THE INVENTION

The Heartwater or cowdriosis is a tick-borne disease caused by an intracellular rickettsial pathogen *Ehrlichia ruminantium* and transmitted by ticks of the genus *Amblyomma*. The disease can cause high mortality rates of up to 90% in susceptible ruminants. Heartwater is endemic in sub-Saharan Africa where it presents a serious constraint to livestock improvement programs. Through its occurrence in the Caribbean, there is significant threat of introducing heartwater into North America, where the presence of competent vectors, *A. cajennense, A. maculatum*, and *A. dissimile* have been confirmed. Additionally, other tick-borne diseases including *Ehrlichia chaffeensis, Ehrlichia. canis, Ehrlichia ewingii, Ehrlichia muris, Anaplasma phagocytophilum, Anaplasma platys*, and *Anaplasma marginale* present serious problems for livestock.

There are no safe or reliable vaccines available for these pathogens. Due to safety concerns associated with the production and manufacture of live attenuated and inactivated vaccines, subunit vaccines are considered appropriate to control the disease in endemic and non-endemic areas. Antigenic diversity amongst different isolates of *E. ruminantium*, resulting in lack of protection between heterologous strains, is the single major obstacle to heartwater vaccine development. However, the observation that inactivated vaccines stimulate protective immunity indicates that the development of a successful recombinant vaccine, using selected *E. ruminantium* genes, is possible. The Major Antigenic Protein 1 (MAP1), encoded by map1 gene, is an immunodominant surface protein of *E. ruminantium* and a target for subunit vaccine development. However, sequence polymorphism of the gene among different isolates suggests that any vaccine based on this gene would have to include variants of all important strains. For the American continent, variants of these genes should ideally be obtained from strains in the Caribbean, which due to geographic proximity, pose the greatest threat of imminent introduction. Previous studies using MAP1 as a subunit vaccine involved DNA vaccine constructs encoding MAP1 of the Crystal Springs isolate from Zimbabwe. This vaccine formulation induced partially protective $T_{H1}$ type immune responses in mice; and a subsequent study to improve protection involved boosting with recombinant MAP1 (rMAP1) resulting in survival rate of mice up to 67%. Protection was associated with induction of $T_{H1}$ type immune responses characterized by production of IgG2a and IgG3 anti-MAP1 specific antibodies. However, when delivered as recombinant protein, MAP1 induced a less protective immune response, which was characterized by anti-MAP1 antibodies of predominantly IgG1 isotype. Although, the mechanism by which the map1 DNA vaccine elicits protection is not fully elucidated, it clearly involves utilization of the host (eukaryotic) expression machinery to generate MAP1 antigen that induces the host anti-pathogen immune response.

MAP1 has been demonstrated to be a glycoprotein, and the protein is expressed in glycosylated form in eukaryotic (endothelial cells) expression systems. Glycosylation of immunodominant surface proteins has also been reported in other *Ehrlichia* species, whereby weak immunoreactivity has been reported for unglycosylated immunodominant proteins of *E. canis* (gp36) and *E. chaffeensis* (gp47). This suggests that glycans are important epitope determinants. The rMAP1 protein used in prime-boost studies were expressed in a prokaryotic (*E. coli*) expression system, which is known to produce nonglycosylated proteins. The present disclosure postulated that lack of protein glycosylation could account for the suboptimal protective immune response observed in mice vaccinated with the rMAP1 protein. The overall hypothesis was that vaccination with glycosylated forms of rMAP1 proteins produced in a eukaryotic (baculovirus) expression system will elicit a more robust immune response that will confer protection against virulent *E. ruminantium* challenge. We have recently reported the successful use of a baculovirus expression system to produce Rift Valley fever virus (RVFV) glycoproteins as constituents of an efficacious vaccine against RVFV infection in a target host. Here, we used a similar baculovirus expression system to produce glycosylated MAP1 proteins from *E. ruminantium* and report for the first time the immunogenicity of a glycosylated rMAP1 subunit vaccine in sheep.

BRIEF DESCRIPTION OF THE INVENTION

To develop a protective DIVA (differentiate infected from vaccinated animals) subunit vaccine for heartwater, we targeted the *E. ruminantium* immunodominant major antigenic protein1 (MAP1) with the hypothesis that MAP1 is a glycosylated protein and glycans contained in the antigenic protein are important epitope determinants. Using a eukaryotic recombinant baculovirus expression system, we expressed and characterized, for the first time, a glycoform profile of MAP1 of two Caribbean *E. ruminantium* isolates, Antigua and Gardel. We have shown that the 37-38 kDa protein corresponded to a glycosylated form of the MAP1 protein, whereas the 31-32 kDa molecular weight band represented the non-glycosylated form of the protein frequently reported in scientific literature. Additionally, the signal peptide common to all *E. ruminantium*, was included and cleavage site identified, which differs from previous attempts to solve this problem. This ensured the glycosylation of the expressed recombinant MAP1 protein. Without being bound to any theory of action, it is postulated that the glycan residues are antigenic determinants and are key to the induction of protective T cell and humoral immune response. It is understood that other methods of glycosylation, such as expression through any mammalian or eukaryotic system, would also be effective. Three groups of sheep (n=3-6) were vaccinated with increasing doses of a bivalent (Antigua and Gardel MAP1) rMAP1 vaccine cocktail formulation with montanide ISA25 as an adjuvant. The glycosylated recombinant subunit vaccine induced *E. ruminantium*-specific humoral and Th1 type T cell responses, which are critical for controlling intracellular pathogens, including *E. ruminantium*, in infected hosts. These results provide an important basis for development of a subunit vaccine as a novel strategy to protect susceptible livestock against heartwater in non-endemic and endemic areas.

The present disclosure provides for an immunogenic composition or vaccine providing protection against *E. ruminantium*. Further, a method for eliciting an immune response in an animal is provided, where the steps include administration of the immunogenic composition or vaccine disclosed herein to an animal or human in need thereof. A method for reducing the incidence and/or severity of clinical signs associated with *E. ruminantium* infection is also provided as an aspect of the present disclosure. Such a method comprises the steps of administration of the immunogenic composition or vaccine providing protection against *E. ruminantium* to an animal or human in need thereof.

Additionally, it is understood that other immunogenic compositions and vaccines against other pathogens, and especially tick-borne pathogens, could be made using the same antigenic protein glycosylation approach as that demonstrated herein. For example, the same approach will be used and effective against infection by a pathogen selected from the group consisting of *Ehrlichia chaffeensis, Ehrlichia canis, Ehrlichia ewingii, Ehrlichia muris, Anaplasma phagocytophilum, Anaplasma platys*, and *Anaplasma marginale* (together with *Ehrlichia ruminantium*, referred to as "tick-borne pathogens of the disclosure"). In preferred forms, the glycosylated protein will be a homolog of the MAP1 protein of *Ehrlichia ruminantlium*. Particularly preferred homolog proteins include glycosylated forms of the p30-1 sequence from *Ehrlichia canis*, the p28-Omp19 protein from *Ehrlichia chaffeensis*, and the MSP4 protein from *Anaplasma marginale*. Preferably, the glycosylation would result from the inclusion of the signal peptide of the same pathogen or from *Ehrlichia ruminantium*.

The immunogenic composition or vaccine of the present disclosure is preferably killed/inactivated bacteria, modified live bacteria, a protein of which can be modified, is also provided herewith. In a preferred aspect, the immunogenic composition or vaccine includes a protein subunit selected from the MAP1 protein subunit of *Ehrlichia ruminantium*, the p30-1 protein from *Ehrlichia canis*, the p28-OMP19 protein from *Ehrlichia chaffeensis*, the MSP4 protein from *Anaplasma marginale*, and any combination thereof. In some preferred forms the MAP1 protein will be derived from the Antigua or Gardel strains of *Ehrlichia ruminantium*. In other preferred forms, the protein subunit will be encoded by a nucleotide sequence having at least 80%, at least 90% or least 95%, 96%, 97%, 98%, 99%, or even 100% sequence homology to a nucleic acid sequence encoding any of the protein subunits described herein including the MAP1 protein subunit of *Ehrlichia ruminantium*, the p30-1 protein from *Ehrlichia canis*, the p28-OMP19 protein from *Ehrlichia chaffeensis*, the MSP4 protein from *Anaplasma marginale*, and any combination thereof. In other preferred forms, the nucleic acid is selected from sequences having at least 80%, 90%, 95%, 96%, 97%, 98%, 99%, or even 100% sequence homology with a sequence selected from the group consisting of SEQ ID No. 1, SEQ ID No. 2, SEQ ID No. 10, SEQ ID No. 11, or any combination thereof. In some forms, the immunogenic composition or vaccine includes a protein having at least 80%, 90%, 95%, 96%, 97%, 98%, 99%, or even 100% sequence homology with a sequence selected from the group consisting of the MAP1 protein subunit of *Ehrlichia ruminantium*, the p30-1 protein from *Ehrlichia canis*, the p28-OMP19 protein from *Ehrlichia chaffeensis*, the MSP4 protein from *Anaplasma marginale*, and any combination thereof. In some preferred forms, these sequences have at least 80%, 90%, 95%, 96%, 97%, 98%, 99%, or even 100% sequence homology with a sequence selected from the group consisting of SEQ ID No. 3, SEQ ID No. 4, SEQ ID No. 5, SEQ ID No. 6, SEQ ID No. 7, SEQ ID No. 12, SEQ ID No. 12, and any combination thereof.

In one aspect, the immunogenic composition or vaccine of the present disclosure further comprises at least one additional element. The at least one additional element is preferably selected from, but not limited to, pharmaceutical carriers, adjuvants, pathogens other than the tick-borne pathogens of the disclosure (such as *E. ruminantium*), additional antigens, preservatives, stabilizers, colors, flavors, and combinations thereof. In a further embodiment, the at least one additional element is an antigenic protein or peptide. In such an embodiment, the antigenic protein or peptide can be used as a positive marker for the immunogenic composition or vaccine.

A method for reducing the incidence or severity of clinical symptoms of heartwater or cowdriosis (*E. ruminantium* infection) or infection and clinical symptoms or signs caused by a tick-borne pathogen of the disclosure is also provided. The method preferably includes the steps of administration of the immunogenic composition or vaccine of the present disclosure to an animal or human in need thereof. The dosage is preferably provided in an effective amount. Preferably, clinical symptoms are selected from, but not limited to, death, fever, respiratory distress, which may be exaggerated, paroxysmal convulsions, anorexia, depression, respiratory congestion, friable mucous membranes, respiratory distress, nervous signs, hyperaesthesia, high-stepping stiff gate, exaggerated blinking, exaggerated chewing movements, and diarrhea. The clinical symptoms are preferably reduced in incidence or severity by about 20%, 30%, 40%, 50%, 60%, 70%, 80%, 90%, 95%, or even by 100% when compared to those animals or humans not provided the immunogenic composition or vaccine of the present disclosure.

A method for eliciting an immune response against heartwater or a different disease caused by a tick-borne pathogen of the disclosure is also provided. The method preferably includes the steps of administration of the immunogenic composition or vaccine of the present disclosure to an animal or human in need thereof. The immunogenic composition or vaccine is preferably a subunit; however, the method is not so limited. The composition or vaccine can be administered once or several times. When administered more than once, the second or subsequent doses will be administered at least 2, 3, 4, 5, 6, 7, 8, 9, 10, 11, 12, 13, 14, 15, 16, 17, 18, 19, 20, 21, 22, 23, 24, 25, 26, 27, 28, 29, 30 days, or more after the initial or previous administration. In preferred forms, the immune response will lessen the severity, frequency, and/or duration of at least one clinical sign of the disease by at least 10%, 20%, 30%, 40%, 50%, 60%, 70%, 80%, 90%, 95%, 96%, 97%, 98%, 99%, or even 100% in comparison to a group of animals or humans that did not receive an administration of the vaccine or immunogenic composition.

BRIEF DESCRIPTION OF THE DRAWINGS

FIG. 1 is an illustration of the sequences of the present disclosure, showing the Antigua and Gardel isolates wherein the rectangular box indicates the signal peptide sequence (SEQ ID No. 14) and the underlined portions are the predicted N- and O-linked glycosylation sites. The top (Antigua) sequence is SEQ ID No 2 and the bottom sequence (Gardel) is SEQ ID No. 11;

FIG. 4 is a series of graphs illustrating the results of endpoint titration of MAP1-specific antibody activity in all three vaccine dose groups, exhibited in a time dependent increase in antibody titers, with 28 dpv sera showing highest endpoint titers and overall antibody reactivity showed persistence of MAP1-specific antibody titers in all vaccinated animals through the endpoint;

FIG. 6A is a series of graphs illustrating the percentage of antigen-specific proliferation of $CD4^+$ and $CD8^+$ T-cells in each of the vaccinated groups for the Gardel isolate, where Group D is the control;

DETAILED DESCRIPTION OF THE INVENTION

Figure 2A:
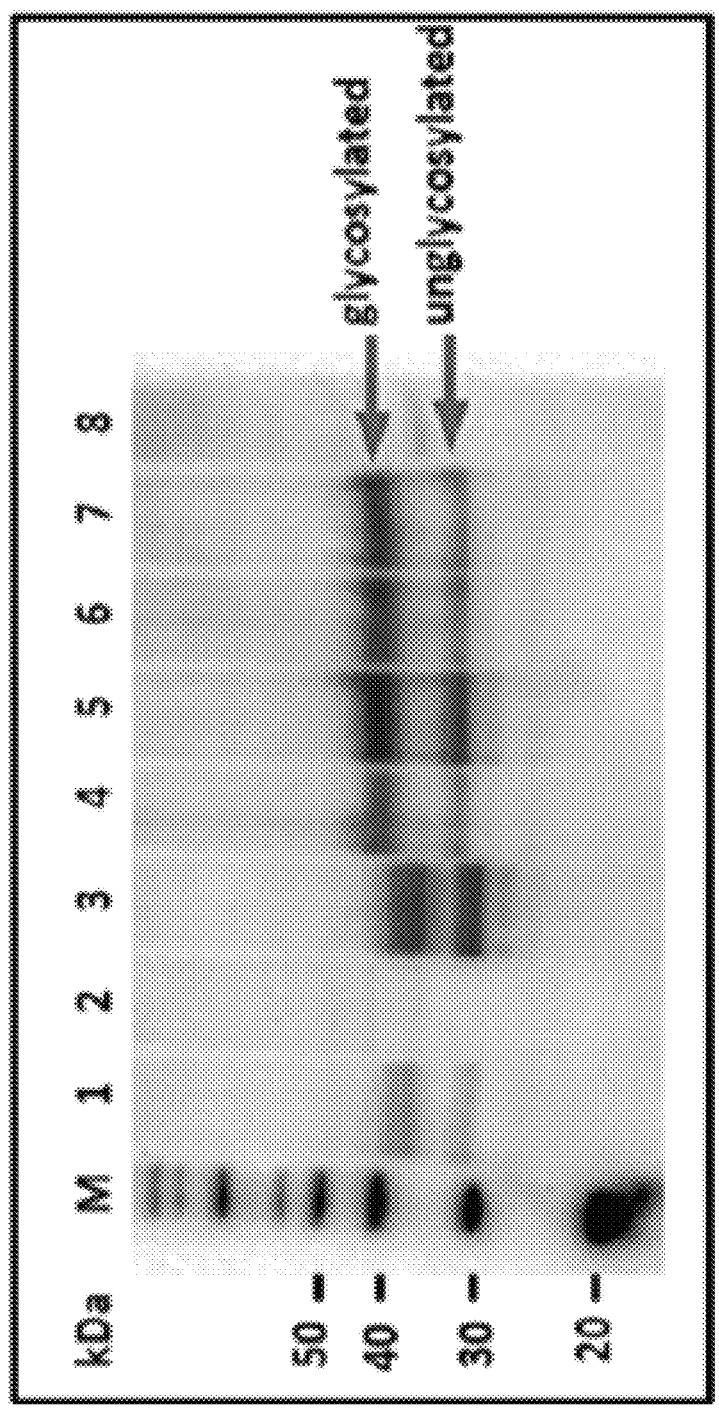
FIG. 2A is a photograph of an electrophoresis gel confirming expression of *E. ruminantium* rMAP1 (Antigua and Gardel isolates) protein in glycosylated form utilizing a eukaryotic expression system and demonstrating a distinct glycosylation profile of the protein.

The present disclosure provides for an immunogenic composition or vaccine providing protection against *E. ruminantium* infection or heartwater, *Ehrlichia chaffeensis, Ehrlichia canis, Ehrlichia ewingii, Ehrlichia muris, Anaplasma phagocytophilum, Anaplasma platys*, and *Anaplasma marginale*. Further, a method for eliciting an immune response in an animal in provided, where the steps include administration of the immunogenic composition or vaccine disclosed herein to an animal or human in need thereof. A method for reducing the incidence or severity of clinical signs associated with a tick-borne pathogen of the disclosure including *E. ruminantium* infection or heartwater, *Ehrlichia chaffeensis, Ehrlichiacanis, Ehrlichia ewingii, Ehrlichia muris, Anaplasma phagocytophilum, Anaplasma platys*, and *Anaplasma marginale* is also provided as an aspect of the present disclosure. Such a method comprises the steps of administration of the immunogenic composition of vaccine providing protection against *E. ruminantium* infection or heartwater or a tick-borne pathogen of the disclosure to an animal or human in need thereof.

The immunogenic composition or vaccine of the present disclosure can either be a killed or live bacterium, a modified live or killed bacterium, a nucleic acid based immunogenic composition; a protein based immunogenic composition; a chimeric composition; or any combination thereof. In a preferred embodiment, the immunogenic composition or vaccine is a protein based subunit vaccine.

In one embodiment, a subunit based immunogenic composition or vaccine is provided. The subunit is preferably encoded by a sequence selected from the group consisting of a modified live or killed sequence of SEQ ID No. 1, SEQ ID No. 2, SEQ ID No. 10, SEQ ID No. 11, and any sequence having at least 80%, at least 90%, or at least 95%, 96%, 97%, 98%, 99%, or even 100%% sequence homology with any one of the recited sequences. Alternatively, the subunit is selected from the group consisting of SEQ ID No. 3, SEQ ID No. 4, SEQ ID No. 5, SEQ ID No. 6, SEQ ID No. 7, SEQ ID No. 12, SEQ ID No. 13, any sequence having at least 80%, at least 90%, or at least 95%, 96%, 97%, 98%, 99%, or even 100%% sequence homology with any one of the recited sequences, or any combination thereof. In preferred forms, the protein subunit is recombinantly-produced.

In a further embodiment, a protein based composition is provided. Preferably, the protein component is selected from, but not limited to, a recombinant protein, a harvested protein, a purified protein, and combinations thereof. In one embodiment, the protein component is a modified MAP1 protein of *E. ruminantium*. In another embodiment, the protein component is a modified homolog protein of MAP1 from a tick-borne pathogen of the disclosure. In another embodiment, the protein component is selected from the group consisting of a modified MAP1 protein of *Ehrlichia ruminantium*, the p30-1 protein from *Ehrlichia canis*, the p28-OMP19 protein from *Ehrlichia chaffeensis*, the MSP4 protein from *Anaplasma marginale*, or any combination thereof. In preferred forms, the modification includes glycosylation such that the modified protein includes more glycosylation than an unmodified protein.

A method for reducing the clinical symptoms associated with heartwater or *E. ruminantium, Ehrlichia chaffeensis, Ehrlichia canis, Ehrlichia ewingii, Ehrlichia muris, Anaplasma phagocytophilum, Anaplasma platys*, or *Anaplasma marginale* infection also provided. The step of the method preferably includes administration of an immunogenic composition or vaccine described herein to an animal or human. The clinical symptoms preferably include, but are not limited to, death, fever, respiratory distress, which may be exaggerated, paroxysmal convulsions, anorexia, depression, respiratory congestion, friable mucous membranes, respiratory distress, nervous signs, hyperaesthesia, high-stepping stiff gate, exaggerated blinking, exaggerated chewing movements, diarrhea, and combinations thereof. The method preferably includes the step of administration of the immunogenic composition or vaccine to an animal or human thereof. Preferably the clinical symptoms associated with heartwater or *E. ruminantium, Ehrlichia chaffeensis, Ehrlichia canis, Ehrlichia ewingii, Ehrlichia muris, Anaplasma phagocytophilum, Anaplasma platys*, and *Anaplasma marginale* infection are reduced in frequency and/or severity by at least 10%, at least 20%, at least 30%, at least 40%, at least 50%, at least 60%, at least 70%, at least 80%, at least 90% or reduced by 100%. This reduction is in comparison to an animal or human not receiving the immunogenic composition or vaccine of the present disclosure. With reference to *E. chaffeensis* in humans, typical symptoms include: fever, headache, fatigue, and muscle aches. Usually, these symptoms occur within 1-2 weeks following a tick bite. With reference to *E. chaffeensis* in dogs, the incubation period for monocytic ehrlichiosis is 8 to 20 days; for granulocytic ehrlichiosis, it is 1 to 14 days after a tick bite. Dogs usually present with fever, lethargy, anorexia, swollen lymph nodes, enlarged spleen, and weight loss. With reference to *E. canis* in dogs, a variety of symptoms during the acute phase of canine monocytic ehrlichiosis can occur, including: fever, lethargy, poor appetite, lymph node enlargement, abnormal bruising and bleeding, chronic eye inflammation, neurologic abnormalities, and occasionally lameness. *E. canis* is so far not considered a human pathogen. With respect to *E. ewingii* in dogs (similar to *E. canis*), clinical illness most often manifests as an acute febrile condition associated with musculoskeletal signs. Reluctance to stand or walk, lameness, a stiff or stilted gait, and joint effusion are common findings in *E. ewingii*-infected dogs and may be quite severe. Lethargy, anorexia, and central nervous system signs (e.g., head tilt, tremors, and anisocoria) may also be present. In humans, typical symptoms of *E. ewingii* infection include: fever, headache, fatigue, and muscle aches. With respect to Anaplasmosis (*A. marginale*), bovine anaplasmosis causes important economic loss in most countries, mainly due to the high morbidity and mortality in susceptible cattle herds. The losses due to anaplasmosis are measured through several parameters: low weight gain, reduction in milk production, abortion, the cost of anaplasmosis treatments, and mortality.

In one aspect of the disclosure, a method for reducing the incidence or severity of clinical symptoms of heartwater or *E. ruminantium, Ehrlichia chaffeensis, Ehrlichia canis, Ehrlichia ewingii, Ehrlichia muris, Anaplasma phagocytophilum, Anaplasma platys,* and/or *Anaplasma marginale* infection is provided. The method includes the step of administering the immunogenic composition or vaccine of the present disclosure to an animal or human. Preferably, the symptoms of heartwater or *E. ruminantium, Ehrlichia chaffeensis, Ehrlichia. canis, Ehrlichia ewingii, Ehrlichia muris, Anaplasma phagocytophilum, Anaplasma platys,* and/or *Anaplasma marginale* infection are selected from, but not limited to, the group consisting of death, fever, respiratory distress, which may be exaggerated, paroxysmal convulsions, anorexia, depression, respiratory congestion, friable mucous membranes, respiratory distress, nervous signs, hyperaesthesia, high-stepping stiff gate, exaggerated blinking, exaggerated chewing movements, diarrhea, and combinations thereof or any of the symptoms described above for any of the other tick-borne pathogens of the disclosure.

The recipient of the composition and method of the present disclosure may be a human or an animal. The animal is preferably selected from, but not limited to porcine, pigs, cows, ruminants, goats, horses, dogs, cats, poultry, and other related wild and domestic animals.

In one aspect, the immunogenic composition may also comprise additional elements, antigens, pharmaceutical carriers, adjuvants, preservatives, stabilizers, or combinations thereof.

Modified or modified live nucleotide sequence will be understood as meaning any nucleotide sequence obtained by mutagenesis according to techniques well known to the person skilled in the art, and containing modifications with respect to the normal sequences according to the disclosure, for example mutations in the regulatory and/or promoter sequences of polypeptide expression, especially leading to a modification of the rate of expression of said polypeptide or to a modulation of the replicative cycle. In some forms, the nucleotide sequence will be used to express a recombinant protein or subunit selected from the group consisting of SEQ ID No. 3, SEQ ID No. 4, SEQ ID No. 5, SEQ ID No. 6, SEQ ID No. 7, SEQ ID No. 12, SEQ ID No. 13, any sequence having at least 80%, at least 90%, or at least 95%, 96%, 97%, 98%, 99%, or even 100%% sequence homology with any one of the recited sequences, or any combination thereof.

Nucleotide, polynucleotide or nucleic acid sequence will be understood according to the present disclosure as meaning both a double-stranded or single-stranded RNA or DNA in the monomeric and dimeric (so-called in tandem) forms and the transcription products of said DNAs.

It must be understood that the present disclosure does not relate to the genomic nucleotide sequences taken in their natural environment, that is to say, in the natural state. It concerns sequences for which it has been possible to isolate, purify or partially purify, starting from separation methods such as, for example, ion-exchange chromatography, by exclusion based on molecular size, or by affinity, or alternatively fractionation techniques based on solubility in different solvents, or starting from methods of genetic engineering such as amplification, cloning and subcloning, it being possible for the sequences of the disclosure to be carried by vectors. Further, the sequences have been altered from what is found in nature to include mutations induced through site-directed mutagenesis or other attenuation techniques, such as serial passaging, further demonstrating that the sequences are made by the hand of man and not found in nature. In some forms, the expression of protein subunits from the nucleotide sequences results in glycosylated forms of the protein, as described above. Such glycosylated forms of the expressed proteins are not found in nature.

The vaccine or immunogenic composition of the present invention does not contain a nucleotide or amino acid sequence found in nature, as it has been constructed by the hand of man. Therefore, the immunogenic composition or vaccine of the present invention is markedly different from what is found in nature. Similar to Example 5 for the Nature-Based Product Examples of eligible subject matter under 35 U.S.C. 101 issued by the US Patent Office in 2014, the immunogenic composition or vaccine of the present invention is like claim 2 of that example because the immunogenic composition or vaccine gene has additional elements, such as the mutations within the sequence or inactivation of the bacteria that provides it with a functionally different characteristic than naturally occurring *E. ruminantium* strains or any of the tick-borne pathogens of the disclosure.

Pharmaceutically acceptable vehicle is understood as designating a compound or a combination of compounds entering into a pharmaceutical composition or vaccine which does not provoke secondary reactions and which allows, for example, the facilitation of the administration of the active compound, an increase in its duration of life and/or its efficacy in the body, an increase in its solubility in solution or alternatively an improvement in its conservation. These pharmaceutically acceptable vehicles are well known and will be adapted by the person skilled in the art as a function of the nature and of the mode of administration of the chosen active compound. At least one pharmaceutically acceptable vehicle can be used with the immunogenic compositions and methods of the present disclosure.

As far as the vaccine and immunogenic composition formulations of the present disclosure are concerned, these can comprise adjuvants of the appropriate immunity which are known to the person skilled in the art, such as, for example, aluminum hydroxide, a representative of the family of muramyl peptides such as one of the peptide derivatives of N-acetyl muramyl, a bacterial lysate, carbomers, montanide ISA25, or alternatively Freund's incomplete adjuvant.

The immunogenic composition and vaccine described herein can be administered by the systemic route, in particular by the intravenous route, by the intramuscular, intradermal or subcutaneous route, or by the oral or nasal, or intranasal route. In a more preferred manner, the immunogenic composition or vaccine composition according to the disclosure will be administered by the intramuscular route, through the food, or by nebulization several times, staggered over time.

Their administration modes, dosages and optimum pharmaceutical forms can be determined according to the criteria generally taken into account in the establishment of a treatment adapted to an animal such as, for example, the age or the weight, the seriousness of its general condition, the tolerance to the treatment and the secondary effects noted. Preferably, the vaccine of the present disclosure is administered in an amount that is protective against heartwater or *E. ruminantium, Ehrlichia chaffeensis, Ehrlichia. canis, Ehrlichia ewingii, Ehrlichia muris, Anaplasma phagocytophilum, Anaplasma platys*, and/or *Anaplasma marginale* infection. Whether the vaccine or immunogenic composition is protective can be determined by one of skill in the art based on whether there is a reduction in the incidence of or severity of clinical symptoms caused by infection by a tick-borne pathogen of the disclosure.

The administration of the immunogenic composition or vaccine according to the present disclosure may be administered one times, two times, three times, four times, five times, six times, seven times, eight times, nine times, or at least 10 times. In one aspect, the immunogenic composition or vaccine of the present disclosure is effective at reducing the severity of and/or incidence of clinical signs of infection after a single dose administration.

For example, the immunogenic composition or vaccine according to the present disclosure may be administered one time or several times, spread out over time in an amount of about 0.1 to 1000 µg per kilogram weight of the animal or human, where values and ranges such as, but not limited to, 0.5 to 800 µg per kilogram weight of the animal or human, 1 to 1000 µg per kilogram weight of the animal or human, 1 to 500 µg per kilogram weight of the animal or human, 1 to 300 µg per kilogram weight of the animal or human, 1 to 200 µg per kilogram weight of the animal or human, 1 to 150 µg per kilogram weight of the animal or human, 1 to 125 µg per kilogram weight of the animal or human, 1 to 100 µg per kilogram weight of the animal or human, 5 µg per kilogram weight of the animal or human, 10 µg per kilogram weight of the animal or human, 15 µg per kilogram weight of the animal or human, 20 µg per kilogram weight of the animal or human, 25 µg per kilogram weight of the animal or human, 30 µg per kilogram weight of the animal or human, 35 µg per kilogram weight of the animal or human, 40 µg per kilogram weight of the animal or human, 45 µg per kilogram weight of the animal or human, 50 µg per kilogram weight of the animal or human, 55 µg per kilogram weight of the animal or human, 60 µg per kilogram weight of the animal or human, 65 µg per kilogram weight of the animal or human, 70 µg per kilogram weight of the animal or human, 75 µg per kilogram weight of the animal or human, 80 µg per kilogram weight of the animal or human, 85 µg per kilogram weight of the animal or human, 90 µg per kilogram weight of the animal or human, 95 µg per kilogram weight of the animal or human, 100 µg per kilogram weight of the animal or human, 125 µg per kilogram weight of the animal or human, 150 µg per kilogram weight of the animal or human, 200 µg per kilogram weight of the animal or human, 250 µg per kilogram weight of the animal or human, 300 µg per kilogram weight of the animal or human, 400 µg per kilogram weight of the animal or human, 500 µg per kilogram weight of the animal or human, 600 µg per kilogram weight of the animal or human, 700 µg per kilogram weight of the animal or human, 800 µg per kilogram weight of the animal or human, 900 µg per kilogram weight of the animal or human, and 1000 µg or more per kilogram weight of the animal or human are envisioned. In other preferred forms, the above amounts are also provided without reference to the weight of the animal or human. Alternatively, the dosage can be between 5-2000 ug, more preferably 10-1800 ug, still more preferably between 15-1600 ug, even more preferably between 20-1400 ug, still more preferably between 25-1200 ug, even more preferably 30 to 1000 ug, still more preferably 35-800 ug, even more preferably 35-600 ug, still more preferably 40-400 ug, even more preferably 45-300 ug, and most preferably 50-200 ug per animal.

According to the present disclosure, the immunogenic composition or vaccine may include an antigen from at least one further pathogen other than *E. ruminantium*, making it a combination vaccine or immunogenic composition. In such an embodiment, an effective amount of a vaccine or immunogenic composition administered provides effective protection including a reduction in the severity or incidence of clinical signs of infection up to and including immunity against infections caused by *E. ruminantium* and at least one further disease-causing organism. In some preferred forms, the combination vaccine or immunogenic composition includes at least one antigen from a group of pathogens selected from the group consisting of *Ehrlichia chaffeensis, Ehrlichia canis, Ehrlichia ewingii, Ehrlichia muris, Anaplasma phagocytophilum, Anaplasma platys*, and *Anaplasma marginale*. In some of these forms, the antigen is similar to the *E. ruminantium* antigen described herein. In some forms, that antigen is the equivalent of the MAP1 protein of *E. ruminantium*. In other preferred forms, the further pathogen is preferably selected from the group consisting of *Rickettsia rickettsia, Rickettsia helevatica, Ehrlichia equi, A. americanum*, and combinations thereof. In still other preferred forms, the other antigen can be from a pathogen that is not from a tick-borne disease.

In another aspect, the present disclosure provides an immunogenic composition or vaccine that is effective against more than one of the tick-borne pathogens of the disclosure. In other words, there is cross protection across the different species. In preferred forms, the cross protection occurs when using a glycosylated form of a protein selected from the group consisting of the MAP1 protein of *Ehrlichia ruminantium*, the p30-1 sequence from *Ehrlichia canis*, the p28-Omp19 protein from *Ehrlichia chaffeensis*, and the MSP4 protein from *Anaplasma marginale*. Use or administration of any of these antigens as described herein will provide some protection including a reduction in the incidence of or severity of clinical signs or symptoms of infection caused by any of these tick-borne pathogens (*Ehrlichia ruminantium, Ehrlichia canis, Ehrlichia chaffeensis*, and *Anaplasma marginale*).

"Homologous nucleotide sequence" or "having sequence homology" in the sense of the present disclosure is understood as meaning a nucleotide sequence having at least a percentage identity with the bases of a nucleotide sequence according to the disclosure of at least 80%, where ranges and values, including but not limited to, from 80% to 85%, 85% to 96%, 80% or 95%, 80%, 81%, 82%, 83%, 84%, 85%, 86%, 87%, 88%, 89%, 90%, 91%, 92%, 93%, 94%, 95%, 95.5%, 96%, 96.5%, 97%, 97.5%, 98%, 98.5%, 99%, 99.5%, 99.9%, and higher are envisioned for the present disclosure, where this percentage being purely statistical and it being possible to distribute the differences between the two nucleotide sequences at random and over the whole of their length.

An "immunogenic composition" as used herein, means an *E. ruminantium, Ehrlichia chaffeensis, Ehrlichia. canis, Ehrlichia ewingii, Ehrlichia muris, Anaplasma phagocytophilum, Anaplasma platys*, and/or *Anaplasma marginale* composition which elicits an "immunological response" in the host of a cellular and/or antibody-mediated immune response to the *E. ruminantium, Ehrlichia chaffeensis, Ehrlichia. canis, Ehrlichia ewingii, Ehrlichia muris, Anaplasma phagocytophilum, Anaplasma platys*, and/or *Anaplasma marginale* sequence, whether the sequence is killed/inactivated, modified live, a subunit of the nucleotide sequence or peptide expressed by that sequence, or in a vector. Preferably, this immunogenic composition is capable of conferring protective immunity against heartwater or *E. ruminantium, Ehrlichia chaffeensis, Ehrlichia canis, Ehrlichia ewingii, Ehrlichia muris, Anaplasma phagocytophilum, Anaplasma platys*, and/or *Anaplasma marginale* infection and the clinical symptoms associated therewith. Preferred subunits are those described herein.

"Sequence Identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, MD 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, even more preferably 95% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, even more preferably 95% identity relative to the reference nucleotide sequence, up to 15%, preferably 10%, even more preferably 5% of the nucleotides in the reference sequence may be deleted or substituted with another nucleotide, or a number of nucleotides up to 15%, preferably 10%, even more preferably 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, even more preferably 95% sequence identity to a reference amino acid sequence, it is intended that the given amino acid sequence of the polypeptide is identical to the reference sequence except that the given polypeptide sequence may include up to 15, preferably up to 10, even more preferably up to 5 amino acid alterations per each 100 amino acids of the reference amino acid sequence. In other words, to obtain a given polypeptide sequence having at least 85%, preferably 90%, even more preferably 95% sequence identity with a reference amino acid sequence, up to 15%, preferably up to 10%, even more preferably up to 5% of the amino acid residues in the reference sequence may be deleted or substituted with another amino acid, or a number of amino acids up to 15%, preferably up to 10%, even more preferably up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

The definition of sequence identity given above is the definition that would be used by one of skill in the art. The definition by itself does not need the help of any algorithm, said algorithms being helpful only to achieve the optimal alignments of sequences, rather than the calculation of sequence identity.

From the definition given above, it follows that there is a well-defined and only one value for the sequence identity between two compared sequences which value corresponds to the value obtained for the best or optimal alignment.

In the BLAST N or BLAST P "BLAST 2 sequence", software which is available in html at the web site ncbi.nlm-.nih.gov/gorf/bl2, and habitually used by the inventors and in general by the skilled man for comparing and determining the identity between two sequences, gap cost which depends on the sequence length to be compared is directly selected by the software (i.e. 11.2 for substitution matrix BLOSUM-62 for length>85).

A "conservative substitution" refers to the substitution of an amino acid residue or nucleotide with another amino acid residue or nucleotide having similar characteristics or properties including size, hydrophobicity, etc., such that the overall functionality does not change significantly.

"Isolated" means altered "by the hand of man" from its natural state, i.e., if it occurs in nature, it has been changed or removed from its original environment, or both. For example, a polynucleotide or polypeptide naturally present in a living organism is not "isolated," but the same polynucleotide or polypeptide separated from the coexisting materials of its natural state is "isolated", as the term is employed herein.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

EXAMPLES

Example 1

Materials and Methods

Production of Recombinant MAP1 Protein
Cloning and Recombinant Protein Expression A recombinant baculovirus expression system was used to express glycosylated MAP1 proteins of the *E. ruminantium* isolates, Antigua and Gardel. Briefly, the complete map1 coding sequences of both isolates were codon-optimized including insertion of a Kozak sequence to achieve high level of target protein expression in *Spodoptera frugiperda*, Sf9, insect cells. The sequences were synthesized and cloned into pUC57 vector by a manufacturer (Genewiz). The resulting recombinant plasmid, pUC57-map1 was used as template in high fidelity PCR using a proof-reading DNA polymerase, Accuprime DNA polymerase (Life Technologies) and gene-specific primers BYF101F 5'-CACCATGAACTGCAAGAAGATCTTCATCACCTCC-3' (SEQ ID No. 8) and BYF102R 5'-GAACACGAAACGACCACCGATCTCGATACC-3' (SEQ ID No. 9). The PCR was performed per manufacturer's instruction. The PCR amplicon was cloned into pFastBac/CT/TOPO to create donor plasmids, pFastBac-Antigua and pFastBac-Gardel, containing map1 coding sequences of Antigua and Gardel, respectively. The recombinant donor plasmids were used to create recombinant bacmid via site-specific transpositioning following transfection into an *E. coli* strain, DH10Bac. Recombinant bacmids were purified using HiPure Plasmid kit (Life Technologies) and used to transfect Sf9 cells to rescue respective recombinant baculoviruses. Recombinant baculoviruses, P2 and above, were used to express recombinant *E. ruminantium* MAP1 in Sf9 cells.

Recombinant Protein Purification

Recombinant MAP1 proteins were expressed with a C-terminal 6xHis-tag fusion protein that allowed purification by affinity chromatography using Ni-NTA superflow resin (Novagen, Rockland, MA). Purification was performed per manufacturer's instruction. Briefly, recombinant baculovirus-infected Sf9 cells expressing recombinant *E. ruminantium* MAP1 proteins were pelleted by centrifugation at 500×g for 5 min. The pellet was resuspended in Ni-NTA binding buffer (300 mM NaCl, 50 mM Na3PO4, pH 8.0, and 10 mM imidazole) containing 1× complete protease inhibitor. Insect Popculture Reagent (Novagen) was then added at 0.05 volumes of original culture volume. The lysate was incubated at room temperature for 15 min and the supernatant further clarified by centrifugation at 1000 rpm for 10 min. The clarified lysate was mixed with previously equilibrated Ni-NTA superflow resin (Novagen-EMD Millipore, Billerica, MA). Binding was performed for 1 hour at 4° C. The suspension was loaded into a column and washed with 10 volumes of wash buffer (300 mM NaCl, 50 mM Na3PO4, pH 8.0, and 20 mM imidazole). Bound protein was eluted with elution buffer (300 mM NaCl, 50 mM Na3PO4, pH 8.0, and 250 mM imidazole). The eluate was dialyzed overnight against storage buffer, phosphate-buffered saline (PBS; pH 7.4), and 5% glycerol. Concentration of the purified proteins was determined using the bicinchoninic acid (BCA) assay (ThermoScientific) at an absorbance of 562 nm, using bovine serum albumin (BSA; Sigma-Aldrich) as the protein standard. Aliquots were stored at −80° C. until used.

Protein Analysis
Western Blot

To assess expression of the target protein, approximately 5 μg of each purified recombinant MAP1 protein (Antigua and Gardel) was subjected to electrophoresis in 12% Bis-Tris polyacrylamide gel in 1× MOPS running buffer (Life Technologies). The proteins were transferred onto PVDF membranes per standard protocols. The membrane was blocked in blocking solution containing 0.1% Tween-20 in PBS (pH 7.4) and 3% bovine serum albumin (BSA) for 1 hour at room temperature or overnight at 4° C. After 3 subsequent washes of 5 min each in 0.1% Tween-20 in PBS, the membrane was incubated with anti-His-(C-Terminal)-HRP monoclonal antibody (Life Technologies) diluted 1:5,000 in blocking solution. Expression of the rMAP1 was further confirmed using mouse anti-*E. ruminantium* monoclonal antibody, 4F10B4 (Abcam) at a dilution of 1:2,000. Following three washing steps, the membrane was probed with a secondary antibody conjugate, goat anti-mouse IgG-HRP (1:5,000) (Santa Cruz, Biotechnologies). Detection of specific reactivity was performed using ECL enhanced chemiluminescent detection system.

Analysis of Protein Glycosylation

To analyze glycosylation of rMAP1 proteins, approximately 50 μg of purified rMAP1 was pelleted at 100,000×g for 30 min at 4° C. The pellet was resuspended in 2 μl of 10× denaturing buffer (New England Biolabs, Ipswich, MA) and 18 μl distilled water. An untreated rMAP1 protein was included as a negative control. The mixtures were heat-denatured at 100° C. for 10 min. Thereafter, the following reagents were added to the reaction: 4 μl of 10× reaction buffer, 4 μl 10% NP40, 4 μl distilled water and 6 μl PNGase F (500,000 U/ml) (New England Biolabs). The mixture was incubated at 37° C. for 1 hour and the reaction stopped by addition of SDS loading buffer. The samples were separated by sodium dodecyl sulfate polyacrylamide gel electrophoresis (SDS-PAGE) in NUPAGE 12% Bis-Tris gels (LifeTech) and transferred onto polyvinylidenedifluoride (PVDF) membranes per standard protocols. The membranes were probed with mouse anti-*E. ruminantium* monoclonal antibodies as described above. Anti-mouse-HRP conjugated secondary antibody (Santa Cruz Biotechnology) was used for detection. Detection of differentially migrating protein bands (treated and untreated rMAP1) was performed to determine glycosylation or non-glycosylation of the MAP1 proteins. Additional glycosylation analysis of rMAP1 was performed by glycan staining using Pierce in-gel glycan staining protocol (Pierce Thermo Scientific) per manufacturer's instructions.

Vaccine Preparation

Recombinant *E. ruminantium* subunit vaccine was composed of purified glycosylated rMAP1 of Caribbean *E. ruminantium* isolates, Gardel and Antigua (a bivalent vaccine). To prepare the vaccine formulations, purified rMAP1 proteins from either isolate were mixed in equal ratios in three different doses: (i) 200 μg (low), (ii) 400 μg (intermediate) and (iii) 600 μg (high). The vaccine was adjuvanted with an montanide ISA25 VG (Seppic, France) per manufacturer's instruction.

Animals and Vaccination

Twenty sheep (Dorper×Katahdin cross) aged 3-4 months were purchased from a private farm in Kansas and assigned to 4 groups. Group A (n=5), group B (n=6), group C (n=6) and Group D (n=3). Pre-vaccination blood was collected in EDTA from all animals and tested by nested pCS20 PCR to confirm their *E. ruminantium*-free status. To assess the appropriate dose response, the vaccine was administered subcutaneously in three different doses. Sheep in group A were vaccinated with 200 μg of rMAP1 subunit vaccine, group B vaccinated with 400 μg, and group C with 600 μg. Group D served as mock-vaccinated control and received adjuvant only. At 21 days post-vaccination, each sheep was boosted with the same vaccine dose with adjuvant administered previously. Animals were bled weekly for serum on day 0 (pre-vaccination), days 7, 14, 21, 28, 35 and 42 post-vaccination. Additionally, at 35 post vaccination, blood was collected in acid citrate dextrose (ACD) tubes for isolation of peripheral blood mononuclear cells (PBMCs) to measure T cell responses as described below. Injection sites and rectal temperatures were examined daily until day 3 post-vaccination for vaccine induced reactions.

Detection of Vaccine-Induced Antibody Responses

Induction of MAP1-specific antibody responses was measured in the animals to assess vaccine-induced seroconversion. An indirect ELISA format using recombinant MAP1 of Antigua and Gardel isolates as diagnostic antigens was used in separate assays. Briefly, flat-bottom 96-well microtiter plates (Nunc, MaxiSorp) were coated with 150 ng per well of recombinant MAP1 antigen in 100 μl of antigen coating buffer (Dulbecco's phosphate buffered saline, DPBS, pH 7.3) and incubated overnight at 4° C. The plates were blocked with PBS pH 7.3, supplemented with 0.1% Tween-20 and 1% non-fat dry milk before adding 100 μl per well of diluted (1:200) serum. Each sample was tested in duplicate and each plate contained duplicate negative and positive control sera obtained from an experimentally infected sheep at Utrecht University in The Netherlands. After washing, plates were incubated with Protein G-HRP (Abcam), diluted 1:50,000 in blocking solution, at 37° C. for 1 hour. Thereafter, 100 μl of substrate buffer containing 0.1 mg/ml 3,3', 5,5'-tetramethyl-benzadine (TMB) (ThermoScientific) and $H_2O_2$ was added and plates were incubated in the dark for 25 min. The reaction was stopped with 2M $H_2SO_4$ and optical densities (OD) were measured at 450 nm using microplate reader Fluostar Omega (BMG Labtech). For each experimental group, the cut-off OD value was determined by addition of 2 standard deviations to the mean OD value of serum obtained from the animals prior to vaccination.

IgG Isotype Response

IgG isotype profiling was performed by determining the end titers of IgG1 and IgG2. Mean endpoint titer was determined for animals in group C (vaccinated with the highest vaccine dose 600 μg of rMAP1 subunit vaccine) using day 28 post vaccination sera. Briefly, 5-fold serial dilutions of test serum were initially made and then incubated with rMAP1 antigen (Gardel) coated in 96-well ELISA plates as described above. After three washings, the plate was incubated for 1 hour with mouse anti-bovine IgG1-HRP (Cat. No. MCA2440P; 1:100 dilution) or mouse anti-bovine IgG2 (Cat. No. MCA626; 1:100) (BioRad); both antibodies showed cross-reactivity with sheep. The mouse anti-bovine IgG2 was further probed with Protein G-HRP (1:50,000) for 1 hr. After washing, reactivity was detected by addition of TMB and $H_2O_2$. The reaction was stopped with 2M $H_2SO_4$ and OD values measured at 450 nm as described above.

Measurement of T-Cell Responses

Antigen-specific CD4+ and CD8+ T cell proliferation and cytokine production was measured in peripheral blood on day 35 post vaccination using protocols we have previously published, modified for use in sheep. Briefly, peripheral blood mononuclear cells (PBMCs) were isolated by density centrifugation, labeled with Cell Trace Violet proliferation dye (Life Technologies) and placed in culture for 6 days with 1 μg/ml of purified rMAP1. Pokeweed mitogen was included as a positive control and used at 1 μg/ml. On day 6, cells were labeled with the Live/Dead Fixable Aqua Dead Cell Stain Kit (Invitrogen) per manufacturer's instructions. Samples were then stained with 10 μg/ml mouse anti-ovine CD4 (clone GC1A, isotype IgG2a), and mouse anti-ovine CD8 (clone CACT80C, clone IgG1), both from Washington State University. After washing, samples were labeled with 5 μg/ml of the following secondary antibodies: anti-mouse IgG2a-Alexa Fluor 488 and anti-mouse IgG1-Alexa Fluor 647 (both from Southern Biotech). Cells were then collected on a BD LSR Fortessa X20 Flow Cytometer and analyzed using FlowJo Software (Treestar Inc.). Live cells were gated based upon expression of CD4+ or CD8+ and proliferation was assessed by dilution of the CellTrace Violet dye. T cell responses were measured by comparing responses to stimulation with rMAP1 from the respective *E. ruminantium* strains to mock-stimulated cultures and results are presented as change-over mock. For intracellular cytokine production, PBMC were stimulated overnight with 1 μg/mL *E. ruminantium* rMAP1-specific antigen in the presence of 10 μg/mL brefeldin A. After 18-24 hours, cells were surface stained as above. After washing, cells were then fixed with the BD Cytofix/Cytoperm kit per manufacturer's instructions and stained with 10 μg/mL mouse anti-ovine IFNγ-PE (BioRad Antibodies). Cells were analyzed via flow cytometry as above, gating on live, IFNγ+ CD4 and CD8 T cells. The frequency of antigen-specific cells was determined by comparing responses to stimulation with rMAP1 from the respective *E. ruminantium* strains to mock-stimulated cultures, and results are presented as change-over mock.

Statistics

Statistical analysis was performed using Prism V6.0f software (Graphpad Software, Inc.). Differences in antibody responses at various post-vaccination time-points between the vaccine-dose groups in response to either vaccine antigens, Antigua or Gardel, were analyzed using a 2-way repeated measures ANOVA. T cell responses were analyzed using a 1-way ANOVA followed by Tukey's Multiple Comparisons post-test analysis.

Results and Conclusions

Expression of Glycosylated Recombinant MAP1 Proteins

Figure 2B:
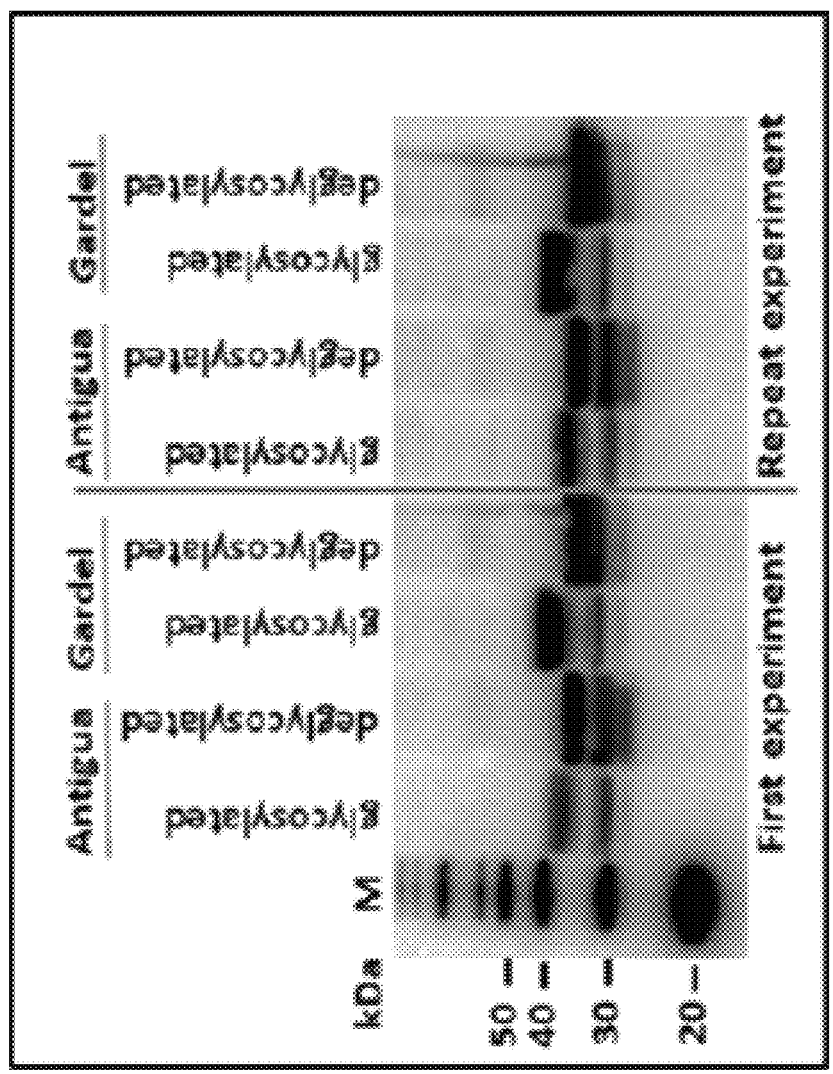
FIG. 2B is a photograph of an electrophoresis gel similar to FIG. 2A.

In silico analysis of MAP1 amino acid sequences of Antigua and Gardel *E. ruminantium* isolates revealed the presence of putative sites for N- and O-linked glycosylation (FIG. 1). To ensure that rMAP1 proteins were expressed in glycosylated form, cloning of map1 gene sequences included signal peptide sequences at the N-terminus of the coding sequence (FIG. 1), which allowed translocation of the protein into the lumen of endoplasmic reticulum where signal peptidases and glycosylation enzymes are located. To rescue respective recombinant baculoviruses for expression of rMAP1 proteins, purified recombinant bacmids encoding mapT genes of either isolate, Antigua and Gardel, were used to transfect Sf9 cells. The recombinant baculoviruses expressed the MAP1 proteins as demonstrated by detection of 32-33 kDa MAP1 proteins of *E. ruminantium*, and a previously undescribed 37-38 kDa protein using anti-His-HRP conjugated and anti-*E. ruminantium* monoclonal antibodies (FIGS. 2A and B). These figures show a glycoform profile. The detection of two (shown here for the first time) shows that MAP1 is expressed in two forms. One of the forms of the protein is glycosylated, which is demonstrated by treating with deglycosylation enzymes that cleave the sugar/glycan residues resulting in a shift in electrophoretic migration. To confirm that the recombinant MAP1 proteins of both isolates were expressed in glycosylated form, a deglycosylation assay was performed. Enzymatic de-glycosylation treatment of rMAP1 proteins of both *E. ruminantium* isolates resulted in reduction in the molecular weight of the upper band demonstrated by a shift in electrophoretic migration (FIG. 2B). The upper band corresponded to a 37-38 kDa glycosylated form of the immunodominant MAP1 (FIG. 2B), whereas the 31-32 kDa molecular weight band represented a non-glycosylated form of the protein (FIG. 2B). An in-gel glycan staining confirmed glycosylation of the rMAP1 protein of both *E. ruminantium* isolates as indicated by the appearance of specific magenta bands in the stained gel.

Analysis of Serological Response

Figure 3B:
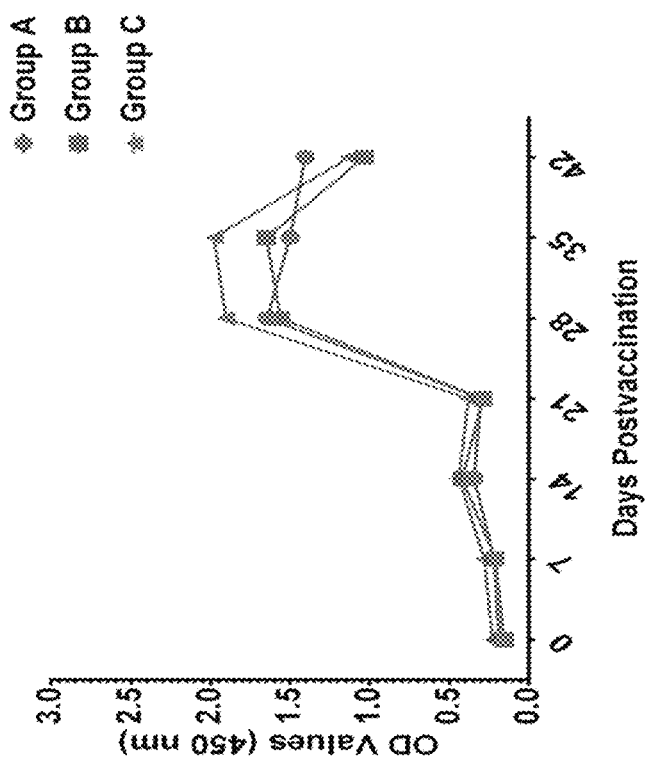
FIG. 3B is a graph showing three groups each having a different dose of the immunogenic composition (low=A (200 ug), intermediate=B (400 ug), and high=C (600 ug), where the graph shows that there was no significant difference between the dose groups in inducing antibody responses, as assessed by the level of IgG antibody responses.
Figure 3A:
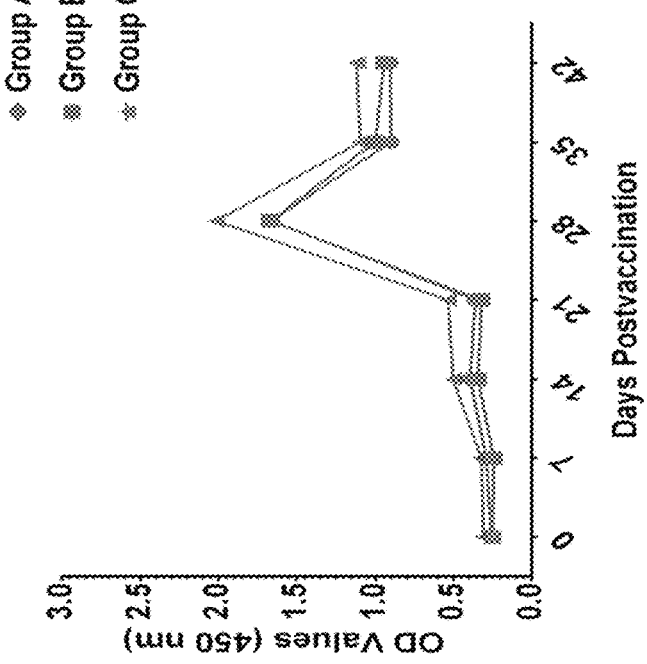
FIG. 3A is a graph showing three groups each having a different dose of the immunogenic composition (low=A (200 ug), intermediate=B (400 ug), and high=C (600 ug), where the graph shows that there was no significant difference between the dose groups in inducing antibody responses, as assessed by the level of IgG antibody responses.
Figure 3C:
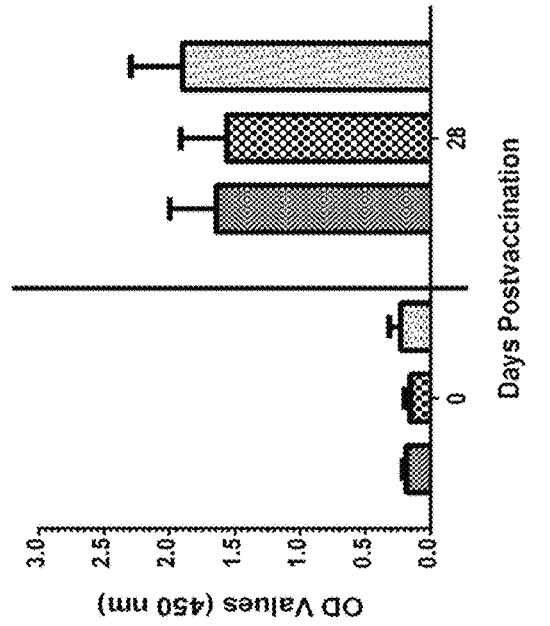
FIG. 3C is a graph showing three groups each having a different dose of the immunogenic composition (low=A (200 ug), intermediate=B (400 ug), and high=C (600 ug), where the graph shows that there was no significant difference between the dose groups in inducing antibody responses, as assessed by the level of IgG antibody responses.
Figure 3D:
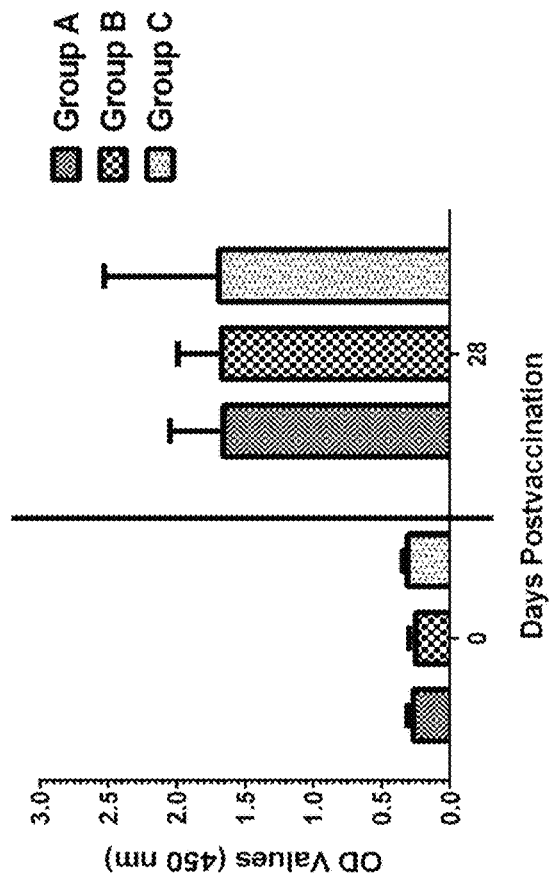
FIG. 3D is a graph showing three groups each having a different dose of the immunogenic composition (low=A (200 ug), intermediate=B (400 ug), and high=C (600 ug), where the graph shows that there was no significant difference between the dose groups in inducing antibody responses, as assessed by the level of IgG antibody responses.
Figure 4A:
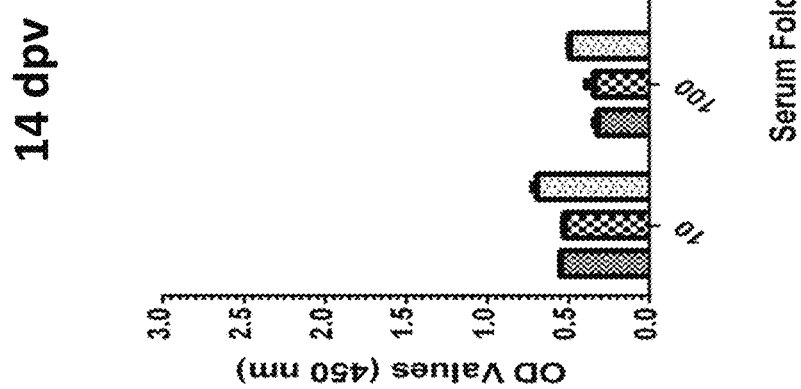
FIG. 4A illustrates the endpoint titration of MAP1-specific antibody activity in all three vaccine dose groups of the Antigua isolate at 7 dpv, exhibited a time dependent increase in antibody titers.
Figure 4B:
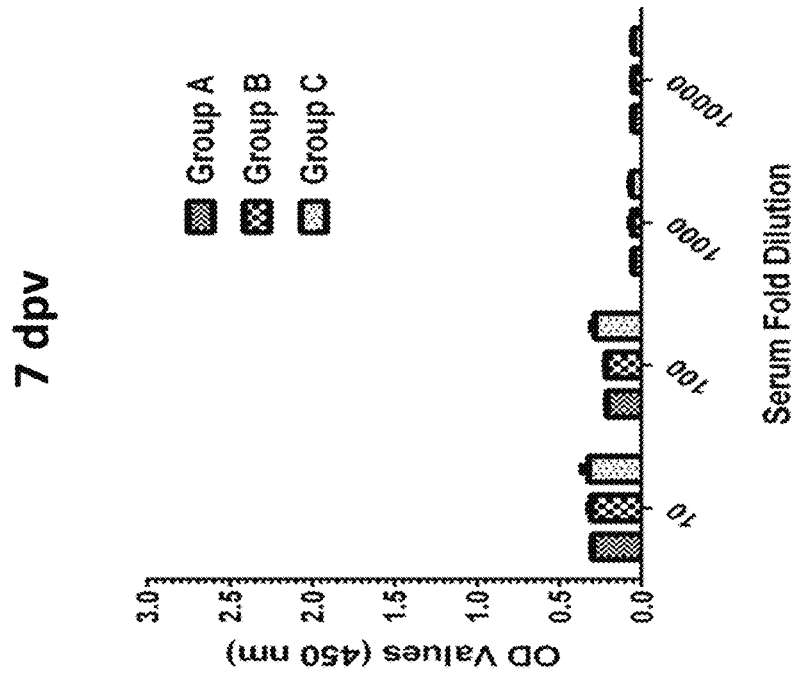
FIG. 4B illustrates the endpoint titration of MAP1-specific antibody activity in all three vaccine dose groups of the Antigua isolate at 14 dpv, exhibited a time dependent increase in antibody titers.
Figure 4D:
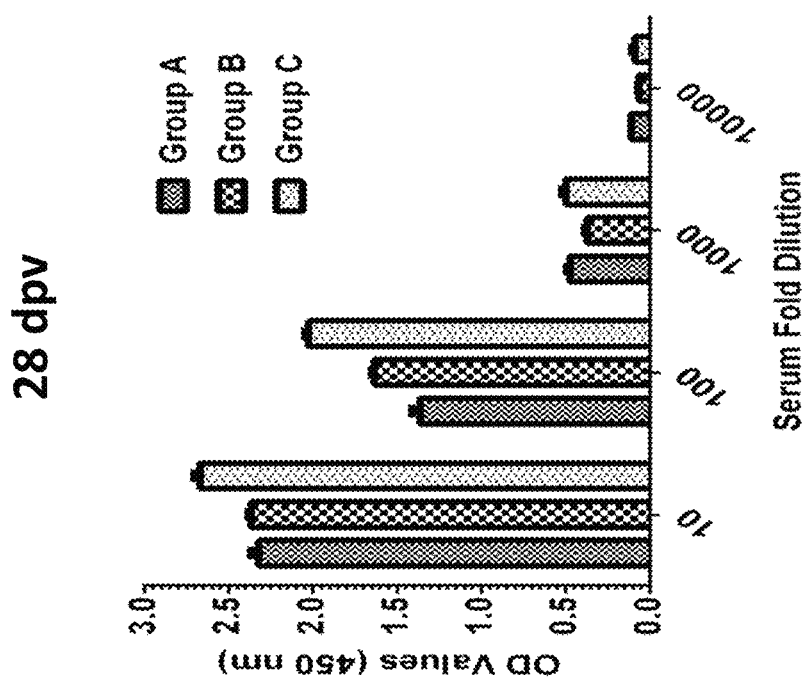
FIG. 4D illustrates the endpoint titration of MAP1-specific antibody activity in all three vaccine dose groups of the Antigua isolate at 28 dpv, exhibited a time dependent increase in antibody titers.
Figure 4C:
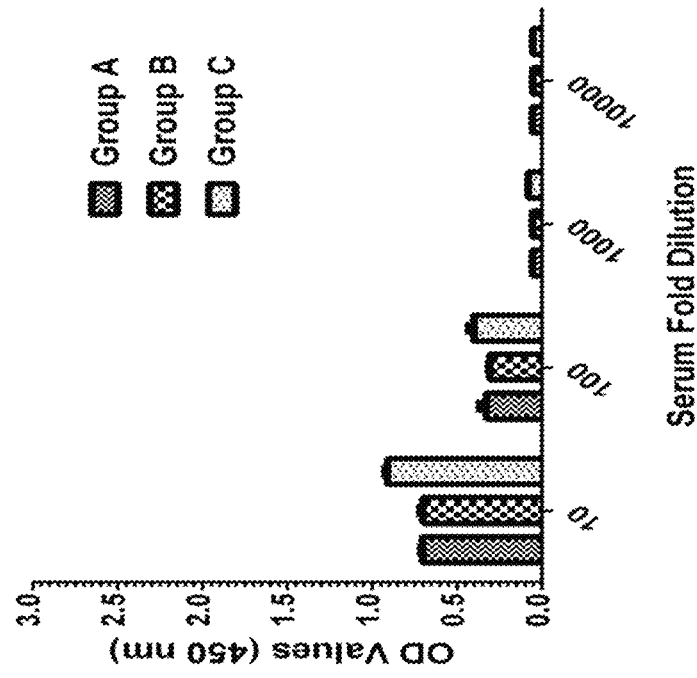
FIG. 4C illustrates the endpoint titration of MAP1-specific antibody activity in all three vaccine dose groups of the Antigua isolate at 21 dpv, exhibited a time dependent increase in antibody titers.
Figure 4F:
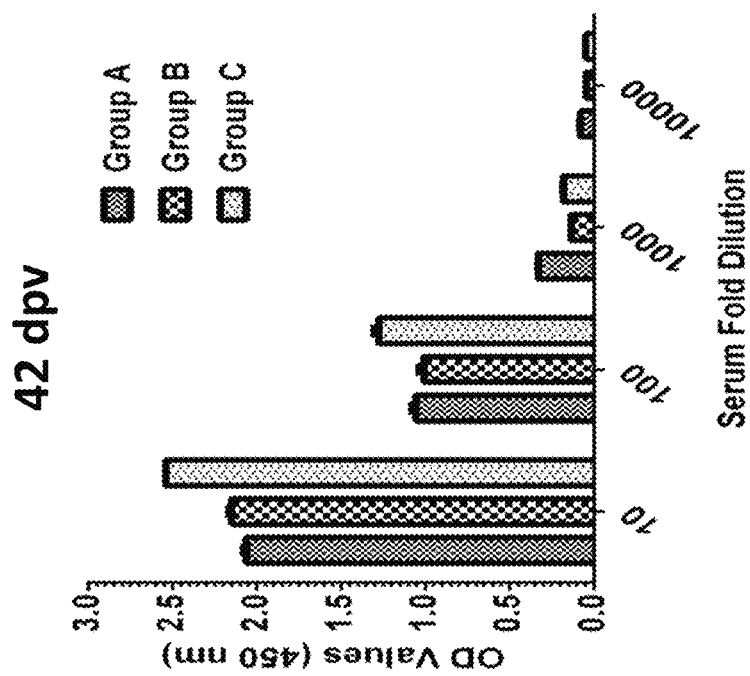
FIG. 4F illustrates the endpoint titration of MAP1-specific antibody activity in all three vaccine dose groups of the Antigua isolate at 42 dpv, exhibited a time dependent increase in antibody titers.
Figure 4E:
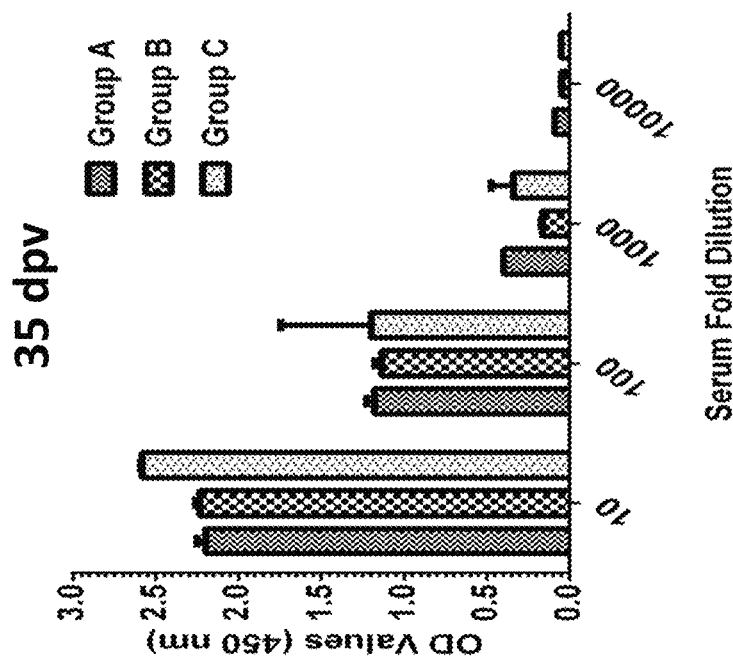
FIG. 4E illustrates the endpoint titration of MAP1-specific antibody activity in all three vaccine dose groups of the Antigua isolate at 35 dpv, exhibited a time dependent increase in antibody titers.
Figure 4H:
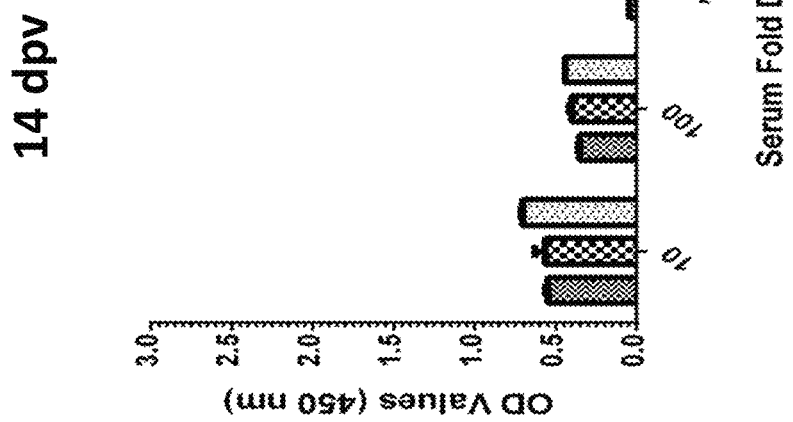
FIG. 4H illustrates the endpoint titration of MAP1-specific antibody activity in all three vaccine dose groups of the Gardel isolate at 14 dpv, exhibited a time dependent increase in antibody titers.
Figure 4G:
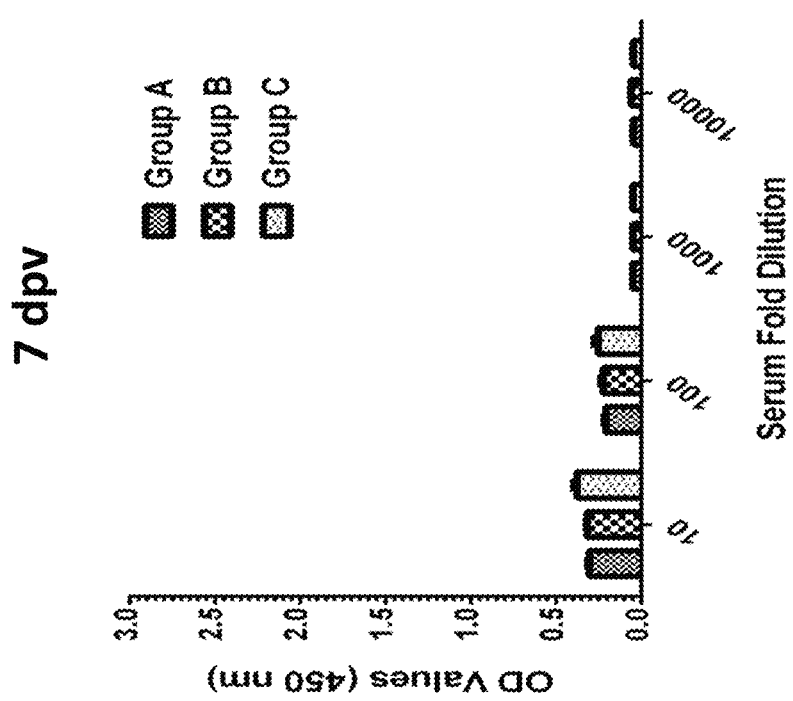
FIG. 4G illustrates the endpoint titration of MAP1-specific antibody activity in all three vaccine dose groups of the Gardel isolate at 7 dpv, exhibited a time dependent increase in antibody titers.
Figure 4J:
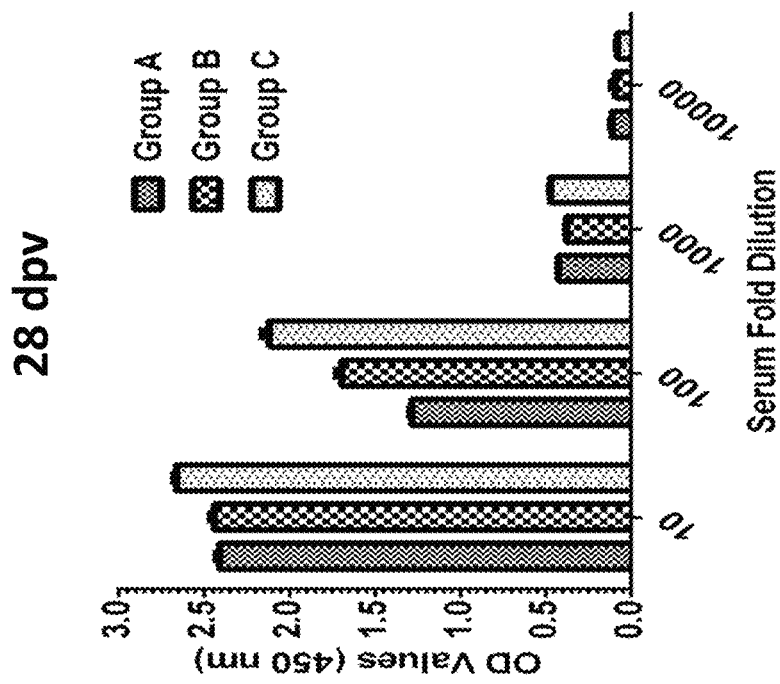
FIG. 4J illustrates the endpoint titration of MAP1-specific antibody activity in all three vaccine dose groups of the Gardel isolate at 28 dpv, exhibited a time dependent increase in antibody titers.
Figure 4I:
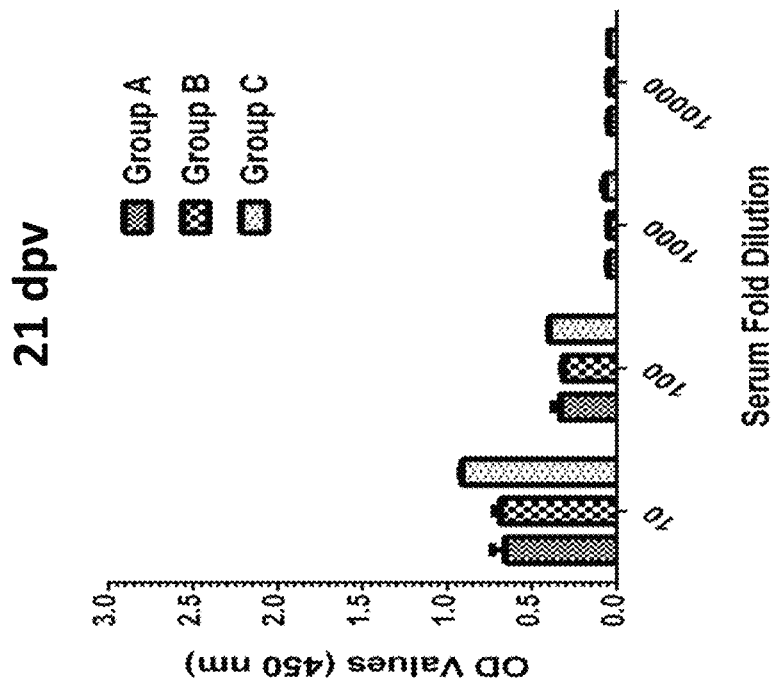
FIG. 4I illustrates the endpoint titration of MAP1-specific antibody activity in all three vaccine dose groups of the Gardel isolate at 21 dpv, exhibited a time dependent increase in antibody titers.
Figure 4L:
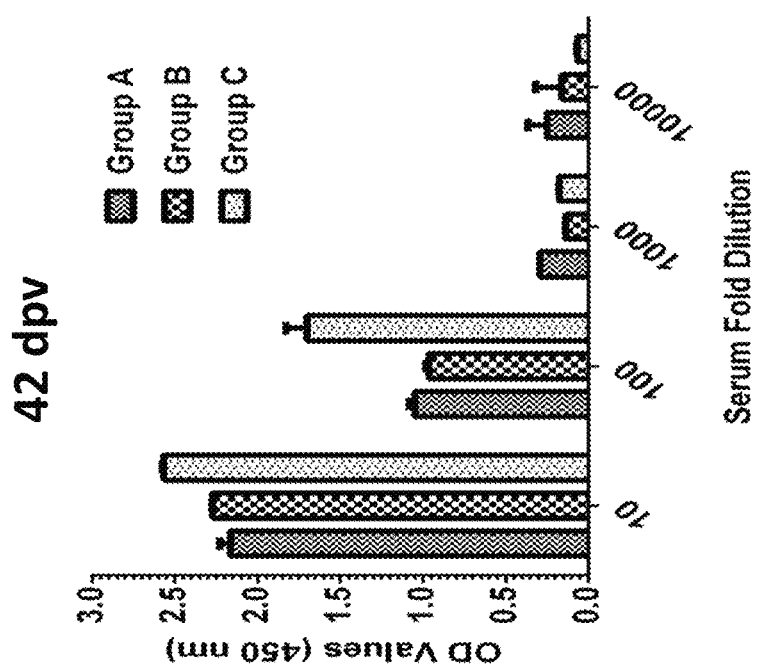
FIG. 4L illustrates the endpoint titration of MAP1-specific antibody activity in all three vaccine dose groups of the Gardel isolate at 42 dpv, exhibited a time dependent increase in antibody titers.
Figure 4K:
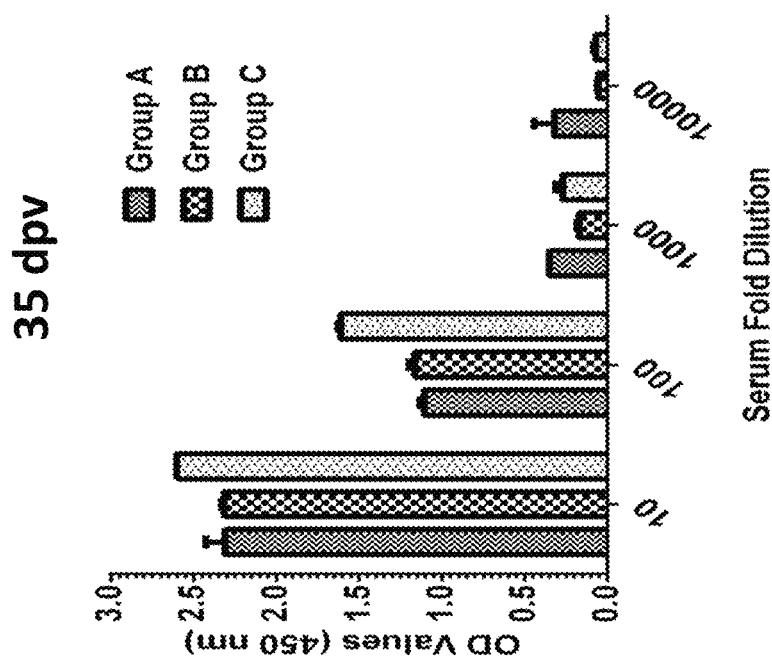
FIG. 4K illustrates the endpoint titration of MAP1-specific antibody activity in all three vaccine dose groups of the Gardel isolate at 35 dpv, exhibited a time dependent increase in antibody titers.

To assess vaccine induced seroconversion and the kinetics of the antibody response, sera were collected from the vaccinated sheep at various time points post-vaccination (day 0, 7, 14, 21, 28, 35, 42) and were tested using MAP1-specific indirect ELISAs. In response to vaccination with the three vaccine dose regimens (Group A=200 μg, Group B=400 μg and Group C=600 μg in equal ratios of rMAP1 proteins of Antigua and Gardel isolates) of the recombinant subunit vaccine, 100% of the animals in all three dose categories seroconverted to both vaccine antigens, Antigua and Gardel rMAP1. Specifically, at day 14 post vaccination all vaccinated animals in the three vaccine dose groups exhibited detectable seroconversion to both vaccine antigens (FIGS. 3A and B). A strong anamnestic response occurred at 28 dpv, which corresponded to peak antibody activity, following administration of a booster at 21 dpv (FIGS. 3A and B). Detectable MAP1-specific antibody titers were maintained in animals in all dose groups until day 42, the study endpoint (FIGS. 3A and B). In response to both vaccine antigens, optical density (OD) values detected at various post-vaccination time-points for the different dose groups were not significantly different (P=0.0606 response to Antigua antigens; P=0.4227, response to Gardel antigen). The magnitude of seroconversion to either vaccine antigen was manifested by marked differences in the absorbance (OD) values in 28 dpv sera (P<0.05) (FIGS. 3C and D).

Figure 5:
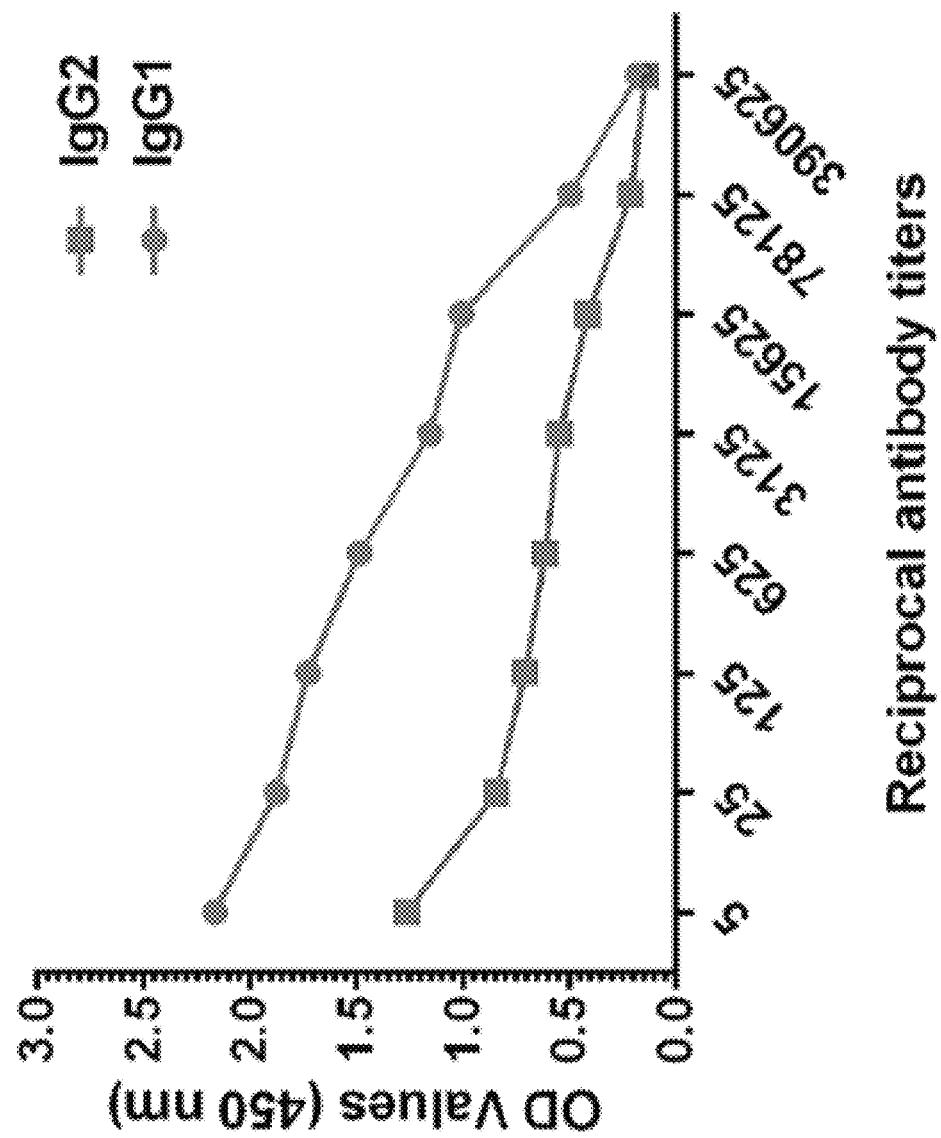
FIG. 5 is a graph illustrating a characterization of the immunoglobulin G (IgG) isotype responses in vaccinated sheep showed induction of both IgG1 and IgG2 antibody responses, with the IgG1 isotype showing comparatively higher titers as determined by endpoint titration.

Endpoint titration of MAP1-specific antibody activity in all three vaccine dose groups exhibited a time-dependent increase in antibody titers, with 28 dpv sera showing highest endpoint titers (FIG. 4). Overall, antibody reactivity data showed persistence of MAP1-specific antibody titers in all vaccinated animals through the study endpoint. Characterization of immunoglobulin G (IgG) isotype responses in vaccinated sheep showed induction of both IgG1 and IgG2 antibody responses, with the IgG1 isotype showing comparatively higher titers as determined by endpoint titration (FIG. 5).

Analysis of CD4+ and CD8+ T Cell Responses

Figure 6B:
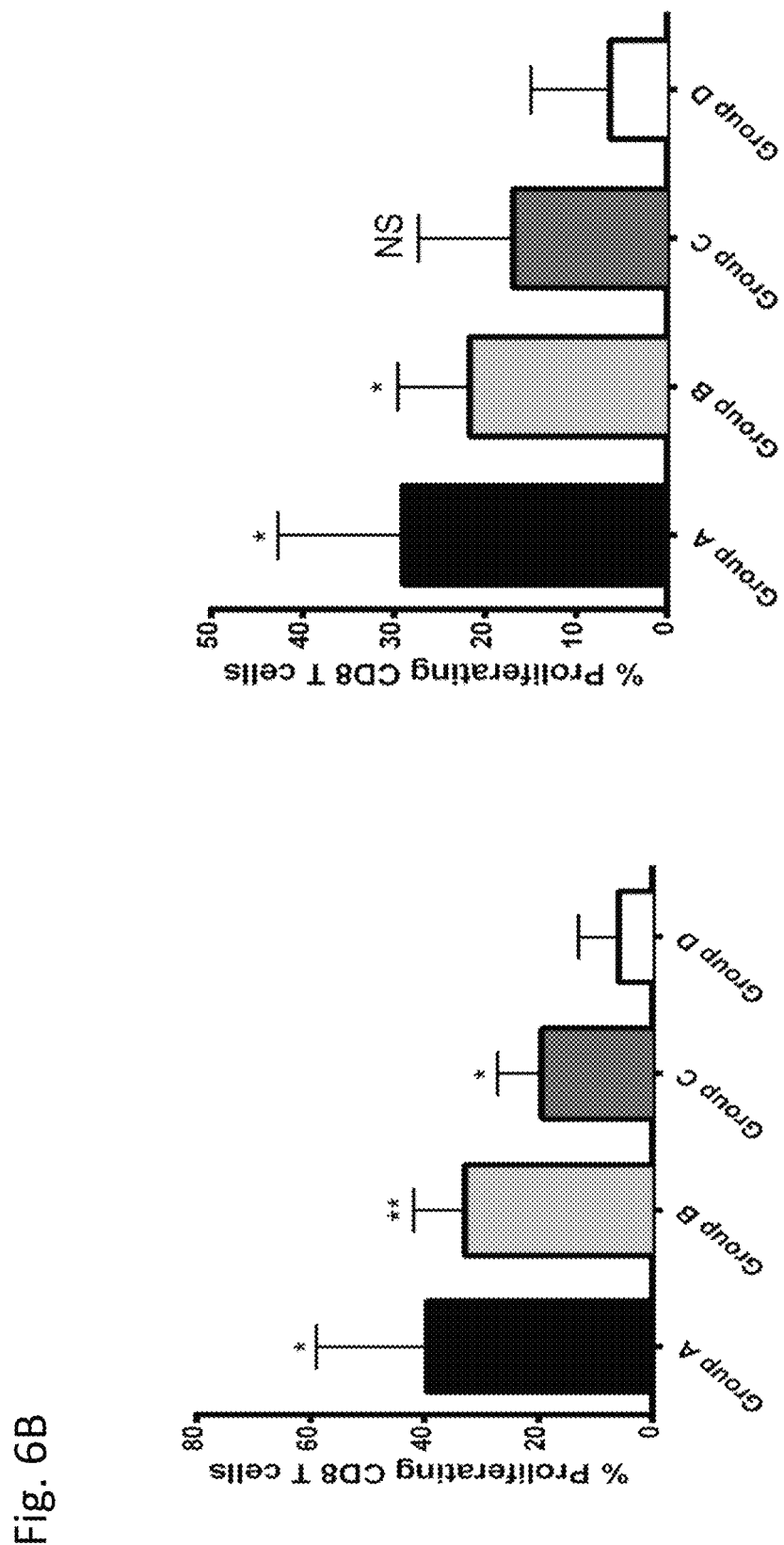
FIG. 6B is a series of graphs illustrating the percentage of antigen-specific proliferation of $CD4^+$ and $CD8^+$ T-cells in each of the vaccinated groups for the Antigua isolate, where Group D is the control.

PBMC isolated from the vaccinated animals demonstrated significant antigen-specific CD4+ and CD8+ T cell proliferation in recall response to either recombinant antigen (Antigua or Gardel rMAP1) (FIGS. 6A and B). Animals vaccinated with 200 μg (group A) of rMAP1 demonstrated the highest frequency of proliferating CD4+ T cells compared to mock vaccinated animals (group D) when stimulated with rMAP1 of either *E. ruminantium* isolates, Antigua or Gardel (P<0.05) (FIG. 6A). The frequency of proliferating CD4+ T cells detected in animals in group B (vaccinated with 400 μg of subunit vaccine) and group C (vaccinated with 600 pg subunit vaccine) was not statistically different from the mock-vaccinated control group D (P>0.05) (FIG. 6A). Furthermore, vaccinated animals in groups A, B and C exhibited a higher frequency of proliferating CD8+ T cells following antigenic stimulation with Antigua rMAP1 than mock-vaccinated control group D (P<0.05) (FIG. 6B). Vaccinated animals in groups A and B also exhibited higher percentage proliferating CD8+ T cells than the mock control group D in response to stimulation with Gardel rMAP1 antigen (P<0.05) (FIG. 6B); however, the frequency of proliferating CD8+ T cells from animals in group C were not statistically different from the mock-vaccinated control group D (P>0.05) (FIG. 6B). Comparison of the frequency of proliferating CD4+ or CD8+ T cells between the various vaccine-dose groups (A, B, C) showed no statistically significant differences (P>0.05).

Figure 7:
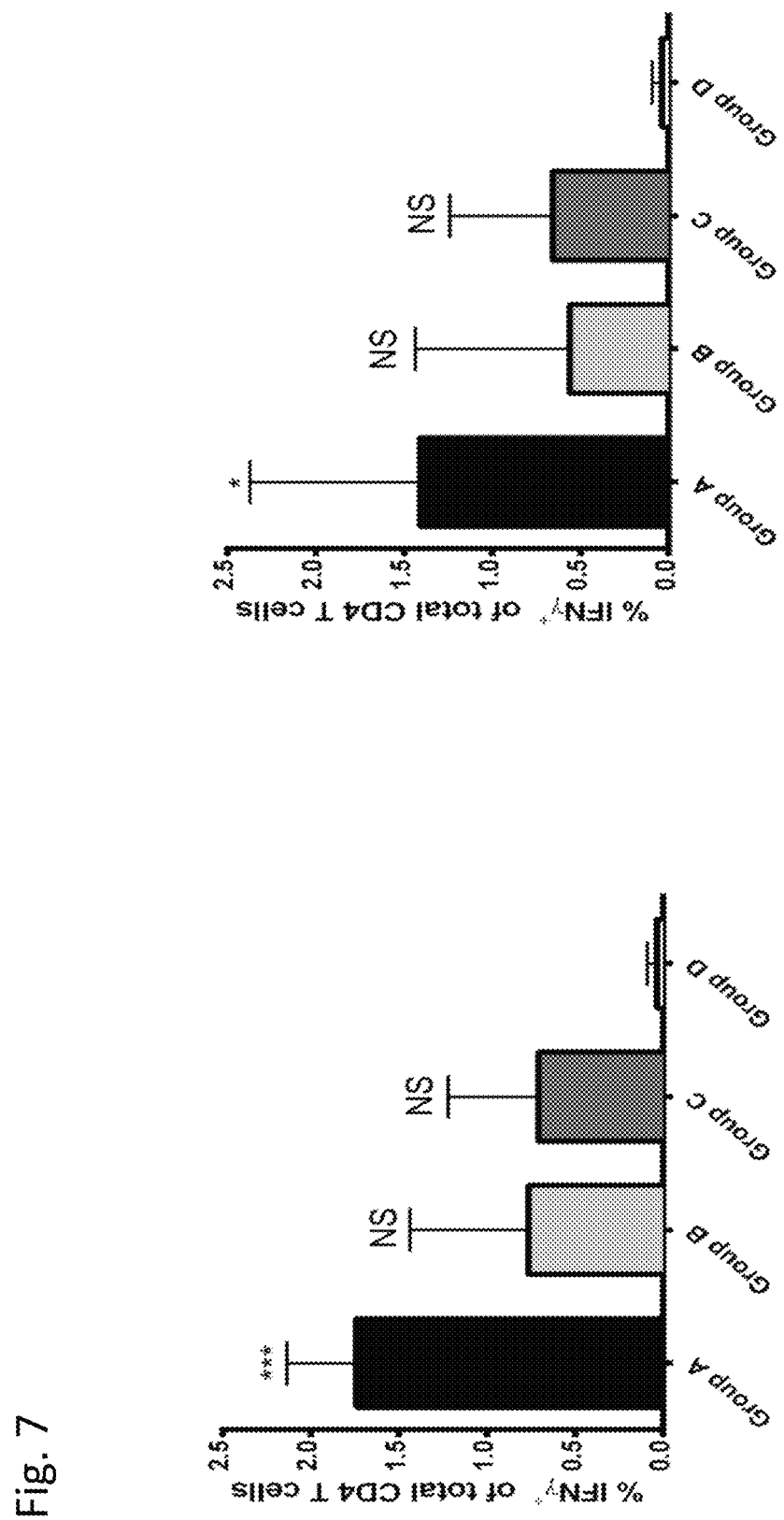
FIG. 7 is a series of graphs illustrating the percentage of $IFN_\gamma$-positive $CD4^+$ cells for each of the vaccination groups, where Group A responded with a higher percentage of $IFN_\gamma$-positive $CD4^+$ cells than any of the other vaccination groups or the control group (Group D)

To assess antigen-specific IFNγ production, CD4+ T cells were subjected to intracellular cytokine staining following antigenic stimulation with Antigua or Gardel rMAP1. Group A animals responded with higher percent of IFNγ-positive CD4+ T cells than the mock-vaccinated control group D (P<0.05) (FIG. 7). The frequency of IFNγ-positive CD4+ T cells detected in groups B and C animals was higher but statistically not different from the control group D animals (P>0.05) (FIG. 7). Comparison of the percent IFNγ-positive CD4+ T cells between the various vaccine-dose groups (A, B, C) revealed no statistically significant differences (P>0.05). Similarly, a comparison of the frequency of IFNγ-positive CD8+ T cells revealed no statistically significant differences between the various vaccine-dose groups (data not shown).

DISCUSSION

Current vaccines developed and evaluated for protecting ruminant livestock against heartwater are based on inactivated and live-attenuated vaccines. These vaccines suffer from low immunogenicity (for killed vaccines), lack of cross-protection and/or safety concerns, especially for use in non-endemic areas. Beside a few sheep studies, most subunit vaccine studies were performed in mouse models. This represents the first study wherein the immunogenicity of glycosylated forms of the major antigenic protein 1 (MAP1) of *E. ruminantium* is assessed in a ruminant model. The *E.*

*ruminantium* MAP1 is an immunodominant membrane protein and considered a good target for vaccine development. Like most membrane proteins with potential sites for glycosylation, in silico analysis of *E. ruminantium* map1 gene revealed putative N-linked and O-linked glycosylation sites (FIG. 1). O-linked sites have been reported to serve as sites for O-linked mannosylation, which has been shown, in eukaryotes, to enhance immunogenicity of membrane proteins. In this study, we confirmed expression of *E. ruminantium* rMAP1 (Antigua and Gardel isolates) protein in glycosylated form utilizing a eukaryotic expression system and demonstrated a distinct glycosylation profile of the protein (FIG. 2). Vaccination of sheep with a subunit vaccine formulation induced both antibody and Th1 T cell responses, which are critical to controlling intracellular pathogens, including *E. ruminantium*, in infected hosts; suggesting that a glycosylated rMAP1 subunit vaccine could be potentially efficacious against virulent heartwater challenge.

Specifically, the recombinant MAP1 subunit vaccine induced a strong Th1 T cell response characterized by increased proliferation of CD4+ and CD8+ T cells, including production of IFN-$_\gamma$, and induction of IgG2 isotype antibodies. The significance of this cellular response in terms of protective immunity in the ruminant host is unknown, as we were unable to perform efficacy testing in this study. However, in a mouse model, a polarized Th1 response characterized by induction of IgG2a and IgG3 antibodies, following a prime-boost vaccination regimen (DNA prime and *E. coli*-expressed rMAP1 boost), was associated with increased protection against virulent heartwater challenge. Increased protection is attributed to in vivo (eukaryotic) expression of glycosylated MAP1 from the DNA vector construct, since immunization with unglycosylated *E. coli*-expressed MAP1 proteins resulted in lower protective efficacy characterized by a Th2 response of predominantly IgG1 isotype. Indeed, the potential role of glycans in antigenicity has been reported for glycoproteins of *E. ruminantium* (MAP1), and antigenically related pathogens, *E. canis* (gp36) and *E. chaffeensis* (gp47), for which glycosylated forms of the proteins exhibited stronger immunoreactivity in comparison to unglycosylated forms. The enhanced T cell response observed in our study could be attributed to the presence of O-linked glycans, by facilitating recognition by mannose receptors on dendritic cells, resulting in efficient uptake, processing, and presentation of antigen to T cells. Taken together, these results suggest that glycan residues in *E. ruminantium* MAP1 proteins are important antigenic determinants. Further studies are required to support this hypothesis including the potential ability to confer broad-spectrum protection amongst antigenically diverse strains of the pathogen.

Although immunity to *E. ruminantium* infection (heartwater), like other intracellular parasites, is mainly cell-mediated, the role of the humoral immune response has not been fully elucidated. In this study, the recombinant MAP1 subunit vaccine also induced strong anamnestic MAP1-specific antibody response in sheep; and even though antibodies produced in response to *E. ruminantium* infection have been reported to not correlate with protective immunity against heartwater, we speculate that their induction is an important vaccine attribute and could play a role as opsonizing agents and contribute to enhancing cell-mediated immunity.

With the aim of assessing the dosage of the subunit vaccine that induces enhanced immune response in sheep, we tested three doses (low, intermediate and high) of the vaccine. There was no significant difference between the different dose groups in inducing antibody responses, as assessed by the level of IgG antibody responses ($P>0.05$) (FIG. 3). In contrast, the dose of the antigen/vaccine appeared to influence the level of cellular responses; showing vaccination with a low dose inducing higher frequency of proliferating CD4+ and CD8+ T cells, including higher levels of secreted cytokine, IFN-$_{65}$, compared to vaccination with intermediate and high doses. The lack of positive correlation is unknown; however, studies in mice have shown that the dose of antigen may be a critical factor in determining what type of immune response will be elicited; with susceptible mice immunized with very low doses of *Leishmania major* demonstrating higher levels of protection than did mice immunized with higher doses of the organism. It has been postulated that very small doses of antigen could imprint the immune response into a Th1-like cell-mediated mode or select T cells with high functional avidity, whereas higher immunizing doses inhibit this response. It is unknown if the comparatively low T cell response observed in the intermediate and high-dose vaccinated groups could be attributed to a similar phenomenon.

Example 2

Recombinant expression of novel *E. ruminantium* type IV and type VI secretion proteins and assessment of their potential use as vaccine and diagnostic antigens.

Materials and Methods

Summary

In this study, we cloned and expressed the genes encoding the *E. ruminantium* type IV (locus tag: ERUM_RS0013 in Welgevonden genome) and type VI (locus tag: ERUM_RS00140 in Welgevonden genome) secretion system proteins using a recombinant baculovirus expression system. We also cloned and expressed the gene encoding the immunodominant major antigenic protein 1 (MAP1) of Kerr Seringe *E. ruminantium* strain (GenBank Accession No. DQ333230) for use as a control in immunoreactivity experiments. To assess the potential use of the recombinant proteins as targets for vaccine and diagnostics development, we examined their reactivity with an antiserum obtained from a sheep experimentally infected with virulent *E. ruminantium* (heartwater agent) by Western blot/immunoblot analysis and indirect enzyme-linked immunosorbent assay (ELISA). Considering that immunoreactive epitopes of *E. ruminantium* MAP1 are conserved in *Ehrlichia canis* (causative agent of canine ehrlichiosis), an antigenically closely related pathogen, we assessed cross-reactivity of the type IV and type VI secretion proteins via indirect ELISA using the recombinant proteins as coating antigens, with antiserum from dogs that tested serologically positive for *E. canis* infection. Serum from a naïve uninfected dog was used as control.

Cloning, Recombinant Protein Expression and Purification

The coding sequences of *E. ruminantium* type IV and type VI secretion proteins, and Kerr Seringe MAP1 were codon optimized and synthesized as insert in pUC57 recombinant plasmid. The sequences were amplified by Accuprime Supermix high fidelity PCR using the respective recombinant plasmids as templates and gene specific primers including the addition of a Kozak sequence. The target PCR amplicons were subsequently cloned into a pFastBac plasmid to create recombinant donor plasmids, pFastBacT4, pFastBacT6 pFastBacMAP1. The donor plasmids were used to create recombinant bacmids via site specific transpositioning using DH10 Bac *E. coli* strain (Life Technologies) according to manufacturer's instruction. The recombinant bacmids were purified and used to transfect *Spodoptera frugiperda* (Sf9) insect cells to rescue the respective recombinant baculoviruses expressing the various target proteins. The proteins were purified using Ni-NTA affinity chromatography and dialyzed against PBS PH 7.4 according to standard protocol (Faburay et al. 2013). Concentration of the purified proteins was measured by BCA method and proteins stored at −80C until used.

Western Blot Analysis

To assess expression of the recombinant proteins, approximately 5 µg of each purified protein was run through a 12% Bis-Tris polyacrylamide gel in 1× 3-(N-morpholino) propanesulfonic acid (MOPS) running buffer, and transfer was performed by electroblotting onto PVDF membranes per standard protocol. The membranes were blocked with 0.1% Tween-20 in PBS (pH 7.4) containing 3% BSA for 1 hr at room temperature. The blot was probed with either anti-His (C-terminal)-HRP monoclonal antibody at 1:5,000 dilution to detect specific recombinant protein expression, or with a primary *E. ruminantium* anti-serum (at 1:50 dilution) obtained from a sheep experimentally infected with virulent isolate of heartwater agent, to detect specific immunoreactivity. Next, the membranes were probed with a Protein G-HRP (1:5,000) or with a secondary antibody, rabbit ant-sheep IgG-HRP (1:2,000). Detection of immunoreactive bands was performed by ECL chemiluminescence detection reagent and visualized using a Biorad.

Enzyme-Linked Immunosorbent Assay

The ELISA plates were coated overnight at 4° C. with approximately 150 ng per well of either purified recombinant protein type IV, type VI or MAP1. The assay was performed as described previously (Faburay et al.,). Briefly, all washing steps were performed three times with 1% Tween 20 in PBS and all samples were tested in duplicate. Following blocking with PBS (pH 7.4) containing 1% skim milk and 0.1% Tween 20 for 15 min at 37° C., the plates were probed at 37° C. for 1 hr with 1:200 dilution of *E. ruminantium*-antiserum obtained from a sheep experimentally infected with virulent heartwater agent, diluted 1:200 (for probing type IV and type VI antigens) or 1:100 (for probing MAP1 antigen), or with 1:200 dilution of *Ehrlichia canis* antiserum obtained from a naturally infected dog, which was confirmed positive by an immunofluorescence antibody test. Negative sheep and dog sera were used as controls. The MAP1 antigen was also probed with 1:200 dilution of antiserum obtained from sheep vaccinated day 42 post vaccination with Gardel-Antigua MAP1 subunit vaccine (Faburay et al., 20017) as positive control. Next, plates were incubated with either 1:5,000 dilution of rabbit ant-sheep-HRP (Invitrogen, Cat. No. 81-8620) for probing sheep antiserum or 1:10,000 dilution of goat anti-dog-HRP (Invitrogen, Cat. No. A18763) for probing *E. canis* dog antiserum. After washing, plates were incubated with TMB substrate for 25 min in the dark at room temperature and reaction was terminated with 2M $H_2SO_4$. Optical density (OD) values were measured at 450 nm wavelengths.

Results

Analysis of Reactivity with *E. ruminantium* Anti-Serum

Figure 8A:
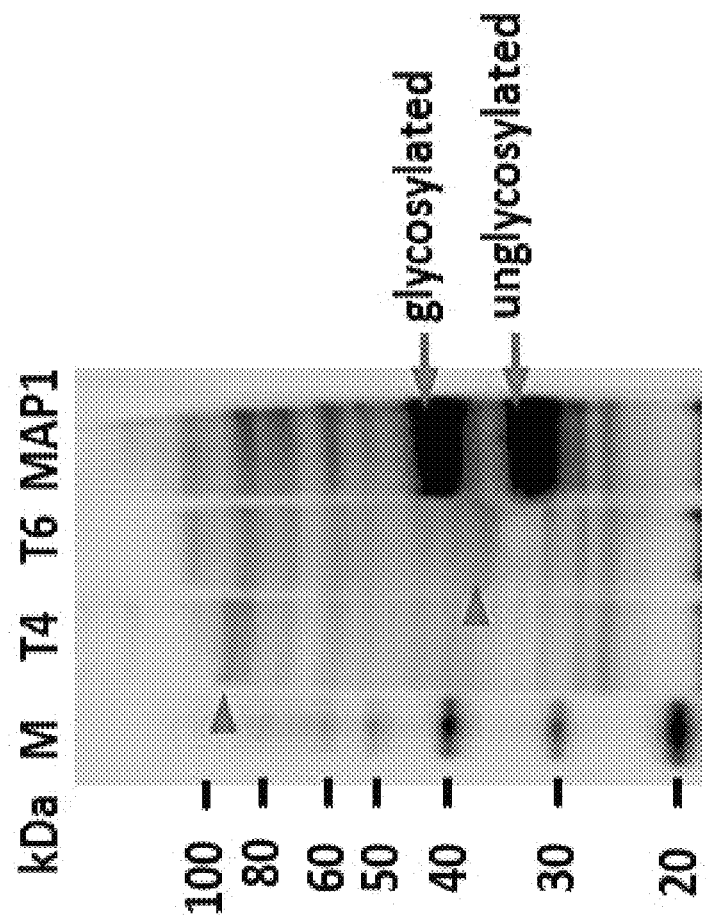
FIG. 8A illustrates a Western blot analysis of recombinant expression and reactivity of ER type IV (T4) and type VI (T6) secretion systems and showing detection of protein expression using mouse anti-His (C-terminal)-HRP monoclonal antibody.
Figure 8B:
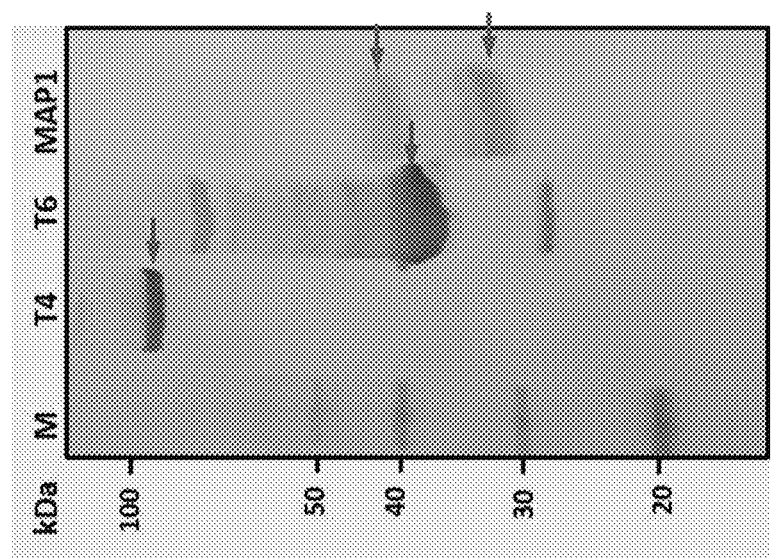
FIG. 8B illustrates a Western blot analysis of recombinant expression and reactivity of specific immunoreactivity of T4 (93 kDa), T6 (38 kDa) and MAP1 (32-39 kDa) using sheep *E. ruminantium* polyclonal antiserum. Arrows indicate specific reactive bands.

The resulted indicated successful expression of the target proteins, ER type IV (T4), type VI (T6) and MAP1 as determined by detection of the estimated molecular size proteins using mouse anti-His (C-terminal)-HRP monoclonal antibody (FIG. 8A). Further probing of the recombinant proteins with ER antiserum from sheep demonstrated reactivity as indicated by detection of estimated molecular size proteins, 93 kDa (type IV), 38 kDa (type VI) and 32-39 kDa (MAP1) corresponding to the expected molecular sizes of the target proteins (FIG. 8B).

Figure 9A:
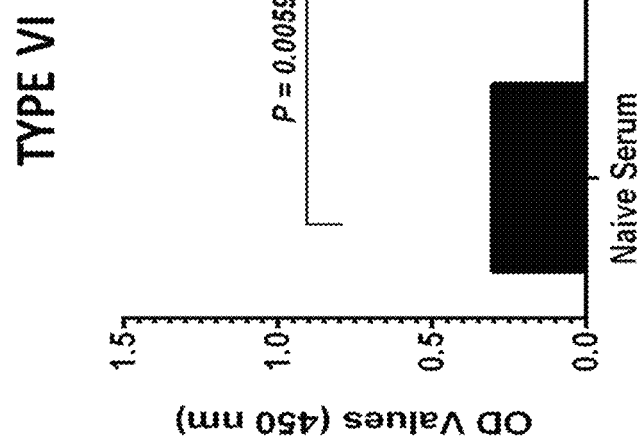
FIG. 9A illustrates an analysis of immunoreactivity of *E. ruminantium* type IV outer membrane protein by indirect enzyme-linked immunosorbent assay (ELISA) using polyclonal ER antiserum obtained from a sheep experimentally infected with virulent heartwater agent. The polyclonal antiserum shows significantly IgG OD readings (higher antibody reactivity ($P<0.05$)) compared to serum obtained from a naïve uninfected sheep. A MAP1 positive control antiserum from sheep vaccinated with a recombinant Gardel-Antigua MAP1 subunit vaccine (Faburay et al., 2017) shows strong reactivity with MAP1 protein.
Figure 9B:
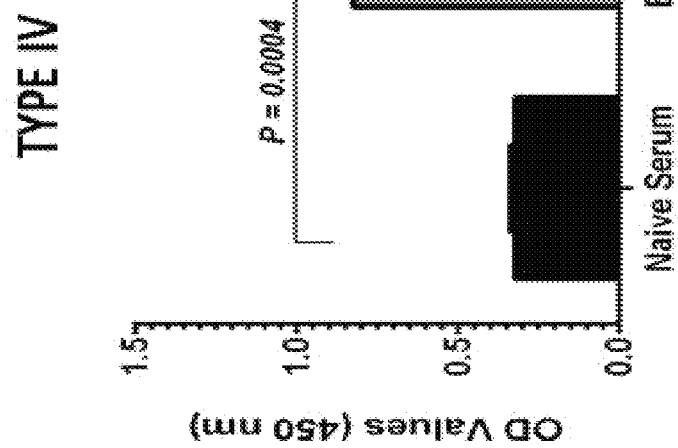
FIG. 9B illustrates an analysis of immunoreactivity of *E. ruminantium* type VI outer membrane protein by indirect enzyme-linked immunosorbent assay (ELISA) using polyclonal ER antiserum obtained from a sheep experimentally infected with virulent heartwater agent. The polyclonal antiserum shows significantly IgG OD readings (higher antibody reactivity ($P<0.05$)) compared to serum obtained from a naïve uninfected sheep. A MAP1 positive control antiserum from sheep vaccinated with a recombinant Gardel-Antigua MAP1 subunit vaccine (Faburay et al., 2017) shows strong reactivity with MAP1 protein.
Figure 9C:
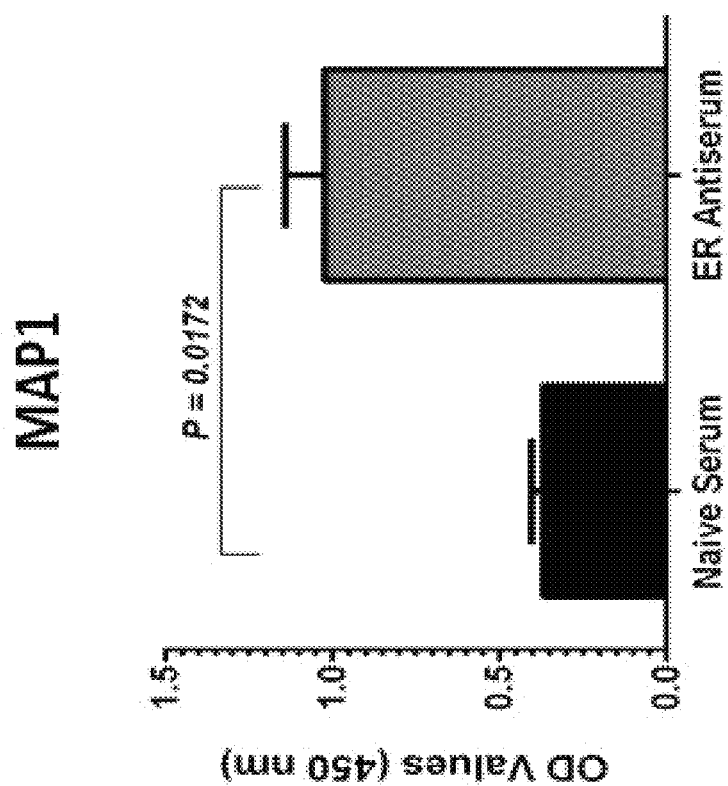
FIG. 9C illustrates an analysis of immunoreactivity of *E. ruminantium* MAP1 outer membrane protein by indirect enzyme-linked immunosorbent assay (ELISA) using polyclonal ER antiserum obtained from a sheep experimentally infected with virulent heartwater agent. The polyclonal antiserum shows significantly IgG OD readings (higher antibody reactivity (P<0.05)) compared to serum obtained from a naïve uninfected sheep. A MAP1 positive control antiserum from sheep vaccinated with a recombinant Gardel-Antigua MAP1 subunit vaccine (Faburay et al., 2017) shows strong reactivity with MAP1 protein.

Further assessment of immunoreactivity of the recombinant protein in indirect ELISA exhibited significantly stronger reactivity of both type IV and type VI secretion proteins ($P<0.05$) with the ER antiserum compared with serum from a naïve uninfected sheep. rMAP1 as a control, demonstrated similar strong reactivity (FIG. 9A, 9B, 9C).

Analysis of Reactivity with *E. canis* Anti-Serum

Figure 10A:
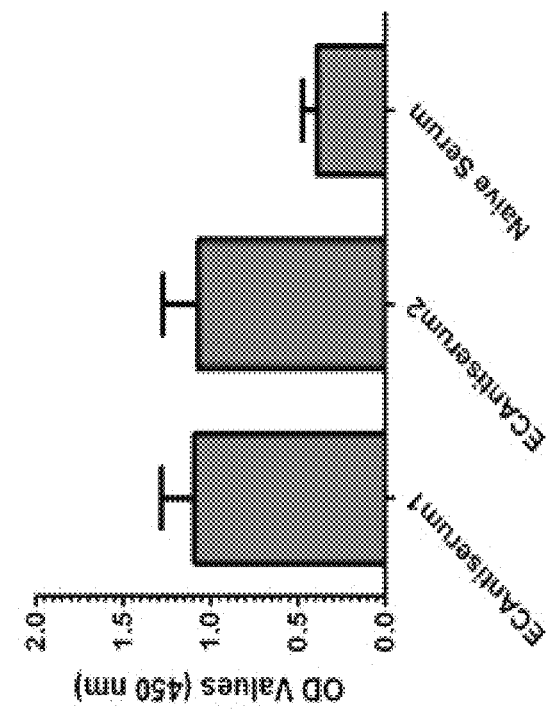
FIG. 10A illustrates an analysis of immunological cross-reactivity of recombinant *E. ruminantium* type IV secretion proteins with *E. canis* anti-sera from infected dogs. Serum from an uninfected dog was used as negative control. Cross-reactivity with recombinant *E. ruminantium* MAP1 is included as a positive control. IgG OD readings the *E. canis*-positive antisera and the naïve uninfected serum are significantly different (P<0.005)
Figure 10B:
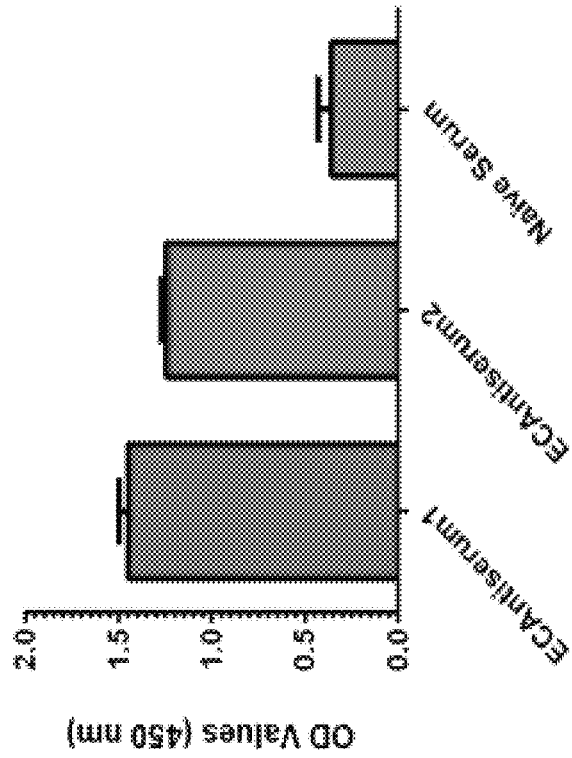
FIG. 10B illustrates an analysis of immunological cross-reactivity of recombinant *E. ruminantium* type VI secretion proteins with *E. canis* anti-sera from infected dogs. Serum from an uninfected dog was used as negative control. Cross-reactivity with recombinant *E. ruminantium* MAP1 is included as a positive control. IgG OD readings the *E. canis*-positive antisera and the naïve uninfected serum are significantly different (P<0.005)
Figure 10C:
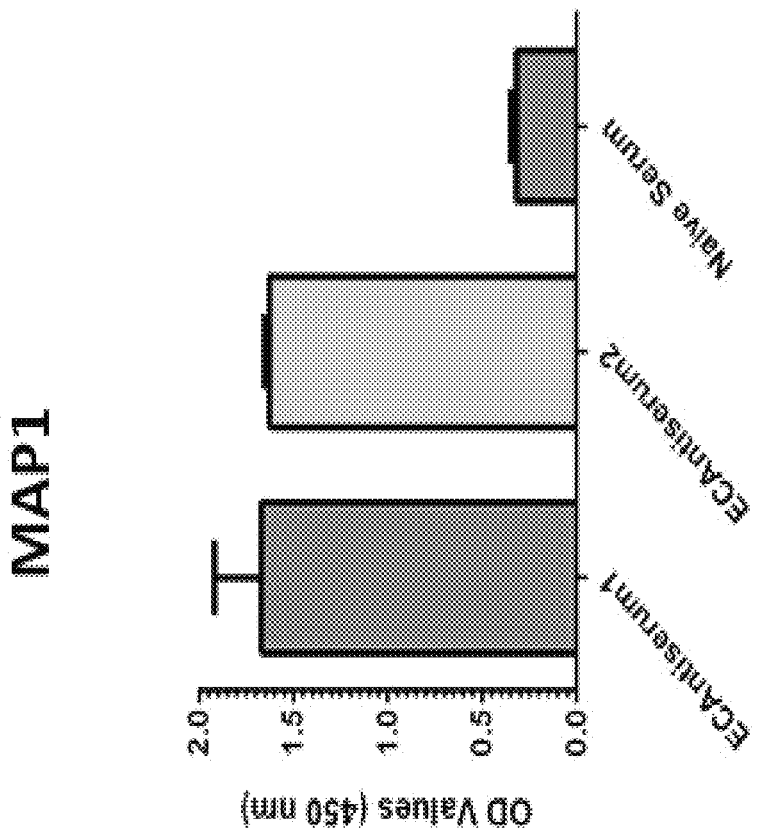
FIG. 10C illustrates an analysis of immunological cross-reactivity of recombinant *E. ruminantium* MAP1 secretion proteins with *E. canis* anti-sera from infected dogs. Serum from an uninfected dog was used as negative control. Cross-reactivity with recombinant *E. ruminantium* MAP1 is included as a positive control. IgG OD readings the *E. canis*-positive antisera and the naïve uninfected serum are significantly different (P<0.005)

To analyze potential cross-reactivity between *E. ruminantium* type IV and type VI secretion proteins with *E. canis* antiserum, ELISA plates were coated with either recombinant protein and subsequently probed with antisera obtained from dogs that tested serologically positive for canine ehrlichiosis. The results indicated that both type IV and type VI secretion proteins exhibited significantly higher IgG OD readings with the positive *E. canis* anti-sera than with serum from naïve uninfected dog (FIGS. 10A, 10B, 10C). As expected, IgG OD readings with the control rMAP1 was similarly higher with the positive *E. canis* antisera compared to the naïve control serum (FIGS. 10A, 10B, 10C).

CONCLUSIONS

Demonstration of immunoreactivity of recombinant ER type IV and type VI secretion proteins with antiserum obtained from sheep experimentally infected with virulent heartwater agent presents a strong indication that these proteins are immunogenic and could elicit specific immune responses in sheep. This suggests their potential use as a vaccine and diagnostic target for protection and/or detection of heartwater in susceptible hosts. Detection of cross-reactivity of recombinant proteins with anti-sera from *E. canis* infected dogs suggests conservation of the immunoreactive epitopes in *E. canis*, an antigenically closely related pathogen, and the potential use of these recombinant proteins as subunit vaccine and/or diagnostic antigens for protection and detection of canine ehrlichiosis, respectively, in dogs.

What is claimed is:

1. A composition comprising a recombinant antigenic protein subunit from a tick-borne pathogen selected from the group consisting of *Ehrlichia ruminantium*, *Ehrlichia chaffeensis*, *Ehrlichia canis*, *Ehrlichia ewingii*, *Ehrlichia muris*, *Anaplasma phagocytophilum*, *Anaplasma platys*, *Anaplasma marginale*, and any combination thereof, wherein the subunit has been glycosylated, and further comprising the MAP1 signal peptide from *Ehrlichia ruminantium*, the adjuvant montanide ISA25, and an additional element selected from the group consisting of at least one additional antigen from a pathogen other than one of said tick-borne pathogens, a preservative, a stabilizer, a color, a flavor, and any combination thereof, wherein the recombinant antigenic protein subunit has been glycosylated from expression through a mammalian or eukaryotic system, and wherein said recombinant antigenic protein subunit has at least 90% sequence homology with a sequence selected from the group consisting of SEQ ID No. 3, SEQ ID No. 4, SEQ ID No. 6, SEQ ID No. 7, SEQ ID No. 12, SEQ ID No. 13, and any combination thereof.

2. The composition of claim 1, wherein said signal peptide sequence comprises SEQ ID No. 14.

3. The composition of claim 1, wherein said recombinant antigenic protein subunit has at least 95% sequence homology with a sequence selected from the group consisting of SEQ ID No. 3, SEQ ID No. 4, SEQ ID No. 6, SEQ ID No. 7, SEQ ID No. 12, SEQ ID No. 13, and any combination thereof.

4. A method for reducing the incidence of and/or severity of at least one clinical sign caused by infection from a tick-borne pathogen comprising the step of administering the composition of claim 1 to an animal in need thereof.

5. The method of claim 4, wherein the at least one clinical sign is selected from the group consisting of death, fever, respiratory distress, which may be exaggerated, paroxysmal convulsions, anorexia, depression, respiratory congestion, friable mucous membranes, respiratory distress, nervous signs, hyperaesthesia, high-stepping stiff gate, exaggerated blinking, exaggerated chewing movements, diarrhea, headache, fatigue, muscle aches, lethargy, swollen lymph nodes, enlarged spleen, weight loss, poor appetite, abnormal bruising and bleeding, chronic eye inflammation, neurologic abnormalities, lameness, reluctance to stand or walk, a stiff or stilted gait, joint effusion, central nervous system signs, low weight gain, reduction in milk production, abortion, and any combination thereof.

6. The method of claim 4, wherein the composition is administered together with at least one additional antigen from a pathogen other than *Ehrlichia chaffeensis*, *Ehrlichia canis*, *Ehrlichia ewingii*, *Ehrlichia muris*, *Anaplasma phagocytophilum*, *Anaplasma platys*, *Ehrlichia ruminantium*, or *Anaplasma marginale* or wherein the composition comprising the recombinant antigenic protein subunit is combined with the at least one additional antigen from a pathogen other than *Ehrlichia chaffeensis*, *Ehrlichia canis*, *Ehrlichia ewingii*, *Ehrlichia muris*, *Anaplasma phagocytophilum*, *Anaplasma platys*, *Ehrlichia ruminantium*, or *Anaplasma marginale* prior to administration.

7. A method of making the composition of claim 1 comprising the steps of:
  making a glycosylated recombinant antigenic protein subunit of a tick-borne pathogen selected from the group consisting of *Ehrlichia chaffeensis*, *Ehrlichia canis*, *Ehrlichia ewingii*, *Ehrlichia muris*, *Anaplasma phagocytophilum*, *Anaplasma platys*, *Ehrlichia ruminantium*, and *Anaplasma marginale* comprising the steps of:
  inserting a nucleotide sequence including the coding sequence for the recombinant antigenic protein subunit and a nucleotide coding sequence for the MAP1 signal peptide from *Ehrlichia ruminantium* into a eukaryotic or mammalian expression system;
  wherein the coding sequence for the glycosylated recombinant antigenic protein subunit has at least 95% sequence homology with a sequence selected from the group consisting of SEQ ID No. 1, SEQ ID No. 2, SEQ ID No. 10, SEQ ID No. 11, or a sequence coding for a sequence selected from the group consisting of SEQ ID No. 3, SEQ ID No. 4, SEQ ID No. 12, SEQ ID No. 6, SEQ ID No. 7, SEQ ID No. 13, and any combination thereof; and
  causing the expression system to express the nucleotide sequence and thereby generate a recombinant antigenic protein subunit together with the signal peptide; and
  recovering the expressed recombinant antigenic protein subunit;
  combining the expressed recombinant antigenic protein subunit with the adjuvant montanide ISA25, and an additional element selected from the group consisting of at least one additional antigen from a pathogen other than one of said tick-borne pathogens, a preservative, a stabilizer, a color, a flavor, and any combination thereof to produce said composition.

8. The method of claim 7, wherein the signal peptide comprises SEQ ID No. 14.

9. The method of claim 7, wherein the signal peptide causes the glycosylation of the recombinant protein.

10. A composition comprising a recombinant antigenic protein subunit from a tick-borne pathogen selected from the group consisting of *Ehrlichia ruminantium*, *Ehrlichia chaffeensis*, *Ehrlichia canis*, *Ehrlichia ewingii*, *Ehrlichia muris*, *Anaplasma phagocytophilum*, *Anaplasma platys*, *Anaplasma marginale*, and any combination thereof, wherein the subunit has been glycosylated, the adjuvant Montanide ISA25, and further comprising the MAP1 signal peptide from *Ehrlichia ruminantium* and an additional element selected from the group consisting of at least one additional antigen from a pathogen other than one of said tick-borne pathogens, a preservative, a stabilizer, a color, a flavor, and any combination thereof, wherein the recombinant antigenic protein subunit has been glycosylated from expression through *Spodoptera frugiperda* (Sf9) insect cells, and wherein said recombinant antigenic protein subunit has at least 90% sequence homology with a sequence selected from the group consisting of SEQ ID No. 3, SEQ ID No. 4, SEQ ID No. 5, SEQ ID No. 6, SEQ ID No. 7, SEQ ID No. 12, SEQ ID No. 13, and any combination thereof.

11. The composition of claim 1, wherein the antigenic protein subunit has at least 90% sequence homology with a sequence selected from the group consisting of SEQ ID No. 6, SEQ ID No. 7, and any combination thereof.

12. The composition of claim 10, wherein the coding sequence for the glycosylated recombinant antigenic protein subunit has at least 90% sequence homology with a sequence coding for a sequence selected from the group consisting of SEQ ID No. 6, SEQ ID No. 7, and any combination thereof.

* * * * *